United States Patent
Lubenau

(10) Patent No.: US 10,821,163 B2
(45) Date of Patent: Nov. 3, 2020

(54) PROCESS FOR THE PRODUCTION OF A DNA VACCINE FOR CANCER IMMUNOTHERAPY

(71) Applicant: VAXIMM AG, Basel (CH)

(72) Inventor: Heinz Lubenau, Neustadt an der Weinstrasse (DE)

(73) Assignee: VAXIMM AG, Basel (CH)

( * ) Notice: Subject to any disclaimer, the term of this patent is extended or adjusted under 35 U.S.C. 154(b) by 0 days.

(21) Appl. No.: 16/315,606

(22) PCT Filed: Jul. 12, 2017

(86) PCT No.: PCT/EP2017/067590
§ 371 (c)(1),
(2) Date: Jan. 4, 2019

(87) PCT Pub. No.: WO2018/011289
PCT Pub. Date: Jan. 18, 2018

(65) Prior Publication Data
US 2019/0183996 A1 Jun. 20, 2019

(30) Foreign Application Priority Data
Jul. 13, 2016 (EP) .................................... 16001550

(51) Int. Cl.
*C12N 1/00* (2006.01)
*A61K 39/00* (2006.01)

(52) U.S. Cl.
CPC .. *A61K 39/0011* (2013.01); *A61K 39/001109* (2018.08); *A61K 39/001168* (2018.08); *A61K 39/001182* (2018.08); *A61K 2039/522* (2013.01); *A61K 2039/523* (2013.01); *A61K 2039/53* (2013.01); *Y02A 50/484* (2018.01)

(58) Field of Classification Search
CPC .................................................. A61K 39/0011
See application file for complete search history.

(56) References Cited

FOREIGN PATENT DOCUMENTS

| WO | WO 2013/091898 | 6/2013 |
| WO | 2014/005683 A1 | 1/2014 |
| WO | WO 2014/173542 | 10/2014 |
| WO | WO 2015/090584 | 6/2015 |

OTHER PUBLICATIONS

Boslego et al (Chapter 17, Gonorrhea Vaccines, pp. 211-223, Vaccines and Immunotherapy) (Year: 1991).*
Plotkin et al (Vaccines W. B. Saunders Company, p. 571) (Year: 1988).*
International Search Report and Written Opinion for PCT/EP2017/067590, dated Sep. 4, 2017.

* cited by examiner

*Primary Examiner* — Albert M Navarro
(74) *Attorney, Agent, or Firm* — Dentons US LLP

(57) ABSTRACT

The present invention relates to a method for producing a DNA vaccine for cancer immunotherapy comprising at least the steps of (a) transforming an attenuated strain of *Salmonella* with at least one DNA molecule comprising at least one expression cassette encoding at least one antigen or at least one fragment thereof; (b) characterizing at least one transformed cell clone obtained in step (a); and (c) selecting at least one of the transformed cell clone(s) characterized in step (b) and further characterizing said at least one selected transformed cell clone. The present invention further relates to a DNA vaccine obtainable by the method according to the present invention.

13 Claims, 12 Drawing Sheets
Specification includes a Sequence Listing.

Fig. 1: Overview Drug Product Manufacture

Starting Material: Salmonella typhi Ty21a recipient strain

↓

Competent Salmonella typhi Ty21a strain ← pVAX10.hAntigen (Plasmid-DNA)

↓

Transformed cell clones

↓ ← Characterization and Batch Production Clone Selection

Batch Production Clone

↓

Drug Substance

↓ ← Release Testing

Drug Product

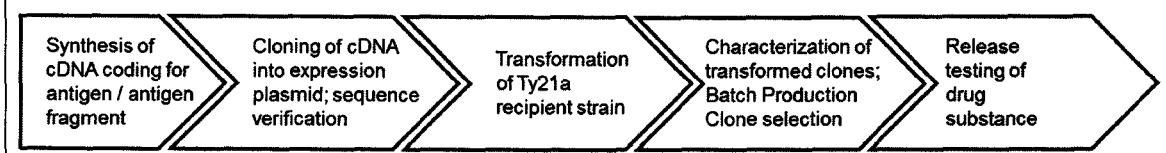
Fig. 2: Flowchart of Drug Product Manufacture

| Fig. 3: Synthesis of Plasmid pVAX10.hAntigen ||| 
|---|---|---|
| | Description of the Process Step | Schematic Drawing of the Process Step |
| 1. | Subdivision of cDNA into oligonucleotides (40 – 50 b); chemical synthesis of oligonucleotides |  |
| 2. | Combination of forward and reverse oligonucleotides and 5'-phosphorylation with T4 polynucleotide kinase |  |
| 3. | Repeated denaturation, annealing and ligation with Taq DNA ligase |  |
| 5. | PCR with outward primers | |
| 6. | Isolation of PCR amplification product and cloning into pVAX10 expression plasmid | |

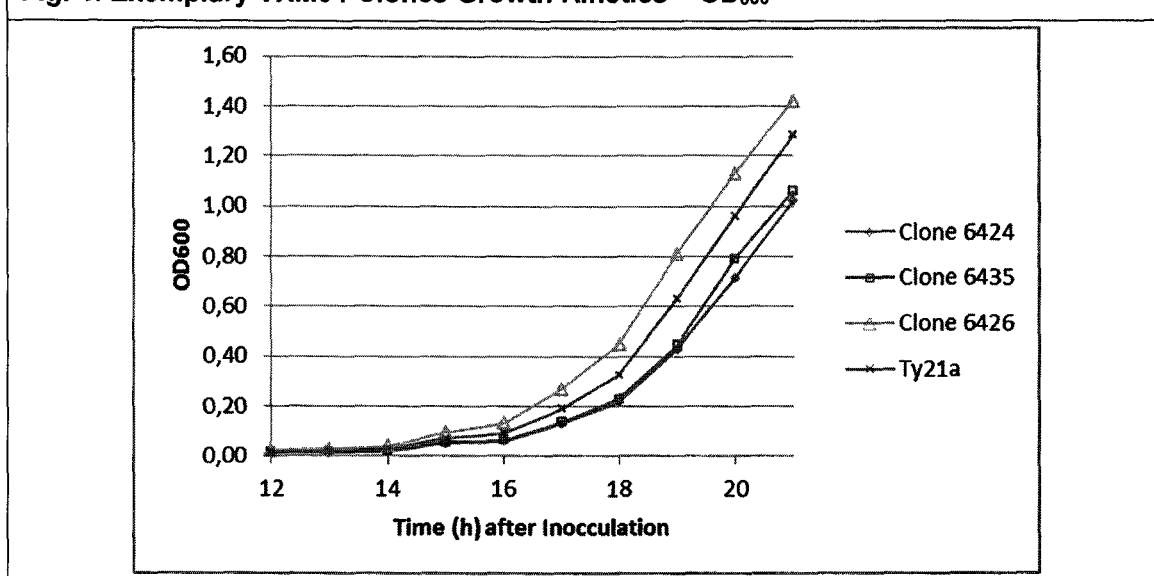
Fig. 4: Exemplary VXM04 Clones Growth Kinetics – $OD_{600}$

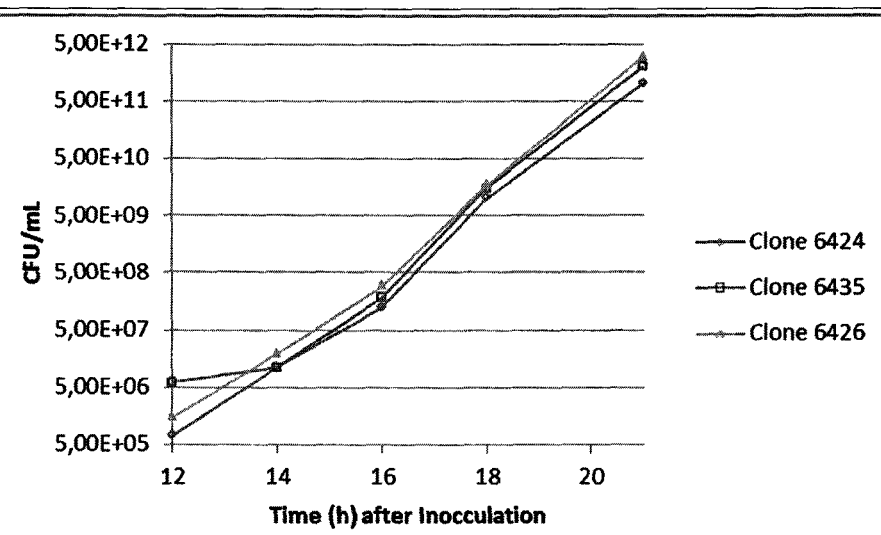
Fig. 5: Exemplary VXM04 Clones Growth Kinetics – CFU/mL

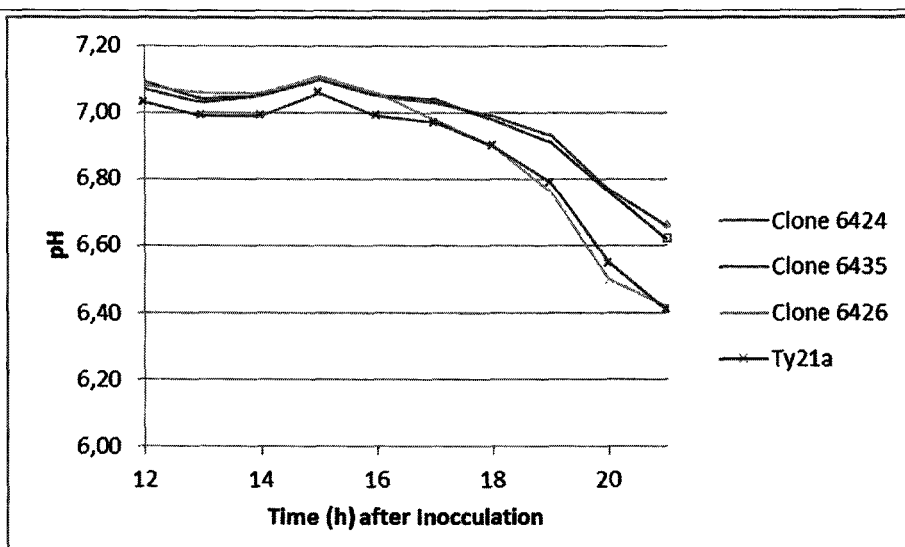
Fig. 6: Exemplary VXM04 Clones Growth Kinetics – pH in Culture Medium

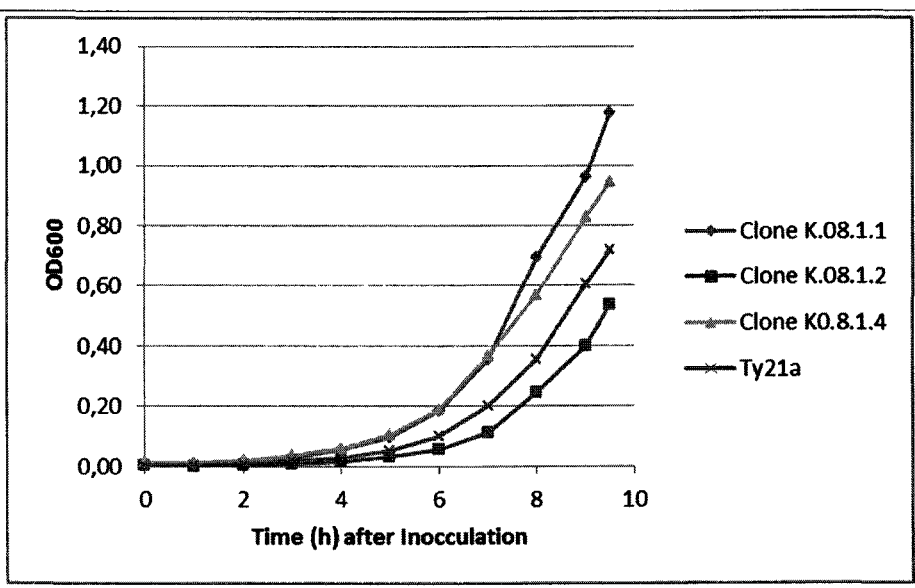
Fig. 7: Exemplary VXM08 Clones Growth Kinetics – $OD_{600}$

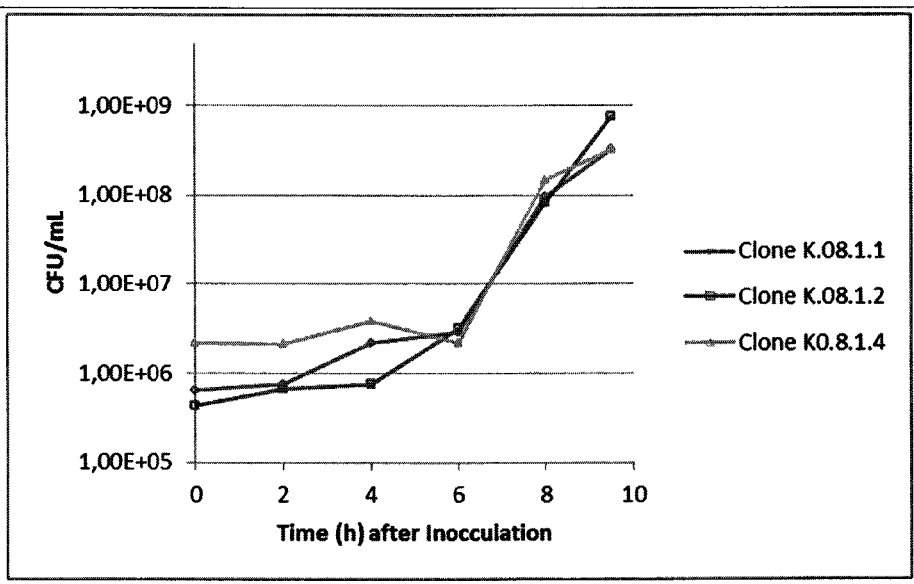
Fig. 8: Exemplary VXM08 Clones Growth Kinetics – CFU/mL

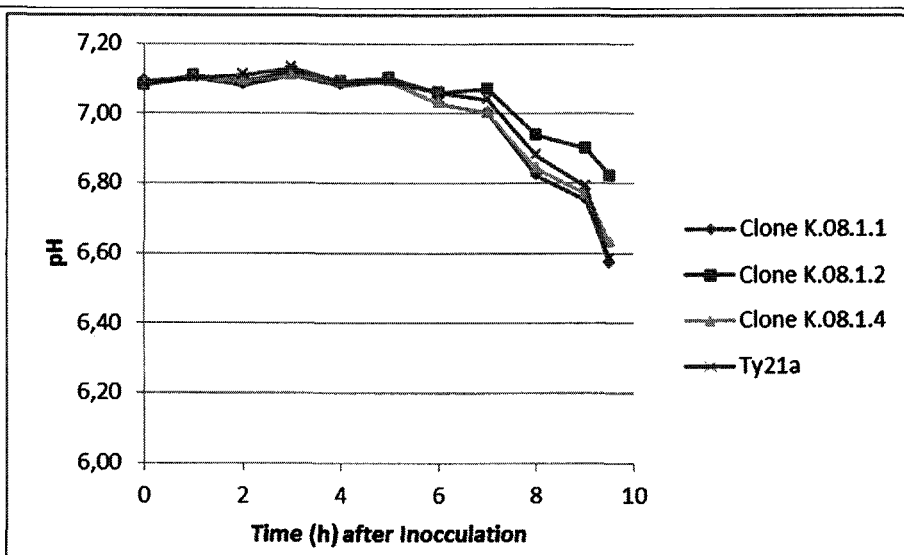
Fig. 9: Exemplary VXM08 Clones Growth Kinetics – pH in Culture Medium

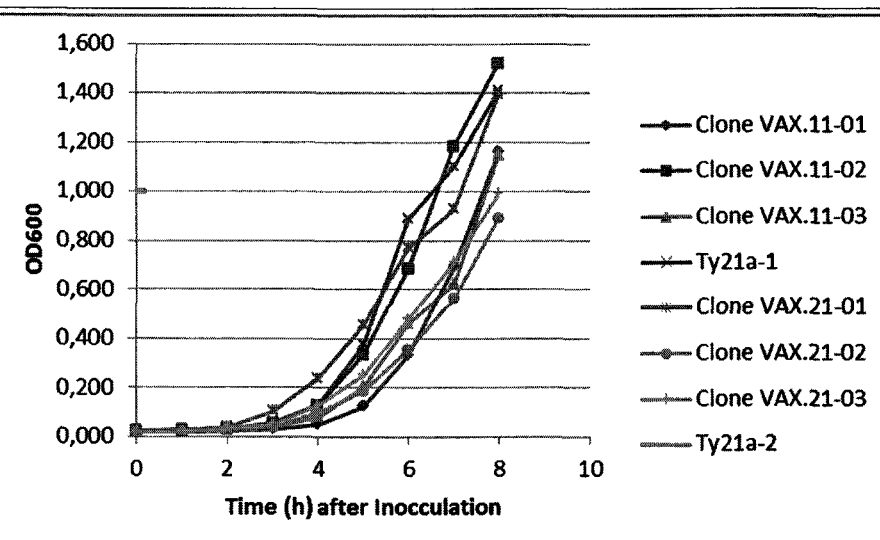
Fig. 10: Exemplary VXM01 Clones Growth Kinetics – $OD_{600}$

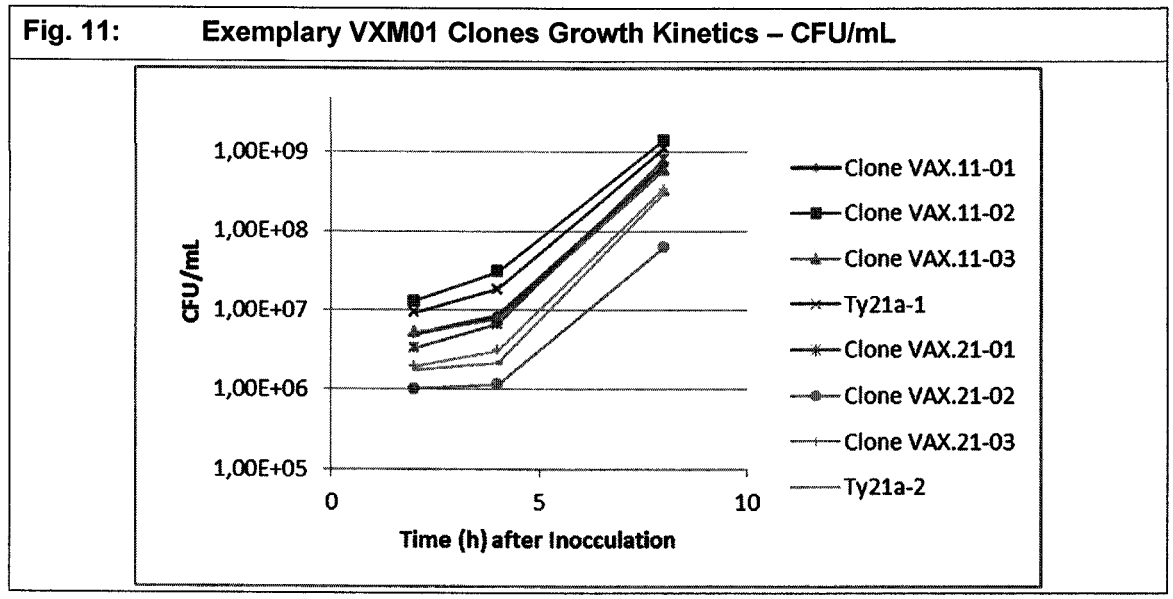
Fig. 11: Exemplary VXM01 Clones Growth Kinetics – CFU/mL

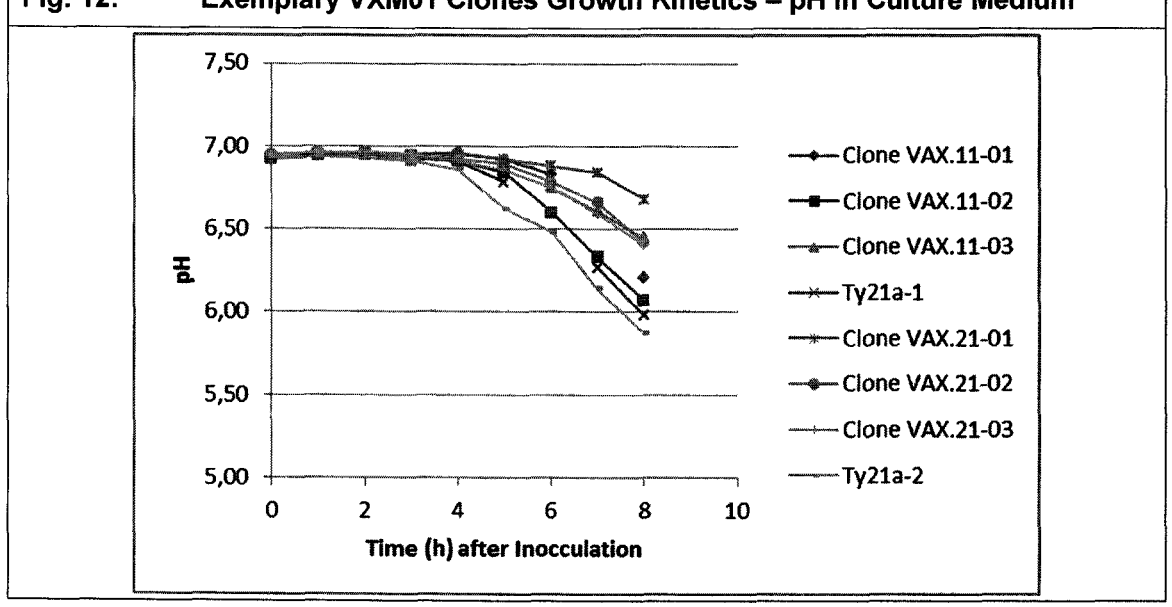
Fig. 12: Exemplary VXM01 Clones Growth Kinetics – pH in Culture Medium

PROCESS FOR THE PRODUCTION OF A DNA VACCINE FOR CANCER IMMUNOTHERAPY

REFERENCE TO RELATED APPLICATIONS

This application is a 371 National Stage application of International Application No. PCT/EP2017/067590, filed Jul. 12, 2017, the entire content of which is herein incorporated by reference in its entirety.

INCORPORATION OF SEQUENCE LISTING

A sequence listing containing the file named "WRSTOO7US_ST25.txt" which is 64 kilobytes (measured in MS-Windows®) and created on Jul. 13, 2016, and comprises 15 sequences, is incorporated herein by reference in its entirety.

FIELD OF THE INVENTION

The present invention relates to a method for producing a DNA vaccine for cancer immunotherapy comprising at least the steps of (a) transforming an attenuated strain of *Salmonella* with at least one DNA molecule comprising at least one expression cassette encoding at least one antigen or at least one fragment thereof; (b) characterizing at least one transformed cell clone obtained in step (a); and (c) selecting at least one of the transformed cell clone(s) characterized in step (b) and further characterizing said at least one selected transformed cell clone. The present invention further relates to a DNA vaccine obtainable by the method according to the present invention.

BACKGROUND OF THE INVENTION

Attenuated derivatives of *Salmonella enterica* are attractive vehicles for the delivery of heterologous antigens to the mammalian immune system, since *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments. Batch preparation costs are relatively low and formulations of live bacterial vaccines are highly stable. Attenuation can be accomplished by deletion of various genes, including virulence, regulatory, and metabolic genes.

The attenuated *Salmonella enterica* serovar *typhi* Ty21a strain (short: *S. typhi* Ty21a), has been accepted for use in humans and is distributed under the trade name of Vivotif® (PaxVax Ltd, UK). This well-tolerated, live oral vaccine against typhoid fever was derived by chemical mutagenesis of the wild type virulent bacterial isolate *S. typhi* Ty2 and harbors a loss-of-function mutation in the galE gene, as well as other less defined mutations. It has been licensed as typhoid vaccine in many countries after it was shown to be efficacious and safe in field trials.

WO 2014/005683 discloses an attenuated strain of *Salmonella* comprising a recombinant DNA molecule encoding a VEGF receptor protein for use in cancer immunotherapy, particularly for use in the treatment of pancreatic cancer.

WO 2013/091898 discloses a method for growing attenuated mutant *Salmonella typhi* strains lacking galactose epimerase activity and harboring a recombinant DNA molecule.

Personalized oncology has the potential to revolutionize the way cancer patients will be treated in the future. The possibility to target patient specific tumor antigens and tumor stroma antigens is attracting increasing attention. A prerequisite for personalized cancer immunotherapy approaches are methods for the fast and cost-effective production of patient-specific cancer vaccines that meet the high medication safety standards.

Thus, there exists a great need for fast and robust manufacturing methods for cancer vaccines, in particular for patient specific cancer vaccines, which has not been met so far.

OBJECTS OF THE INVENTION

In view of the prior art, it is an object of the present invention to provide a novel method for the manufacture of a DNA vaccine for cancer immunotherapy, particularly for personalized cancer immunotherapy. Such a manufacturing method would offer major advantages for improving the treatment options for cancer patients.

SUMMARY OF THE INVENTION

In a first aspect, the present invention relates to a method for producing a DNA vaccine for cancer immunotherapy comprising at least the steps of (a) transforming an attenuated strain of *Salmonella* with at least one DNA molecule comprising at least one expression cassette encoding at least one antigen or at least one fragment thereof; (b) characterizing at least one transformed cell clone obtained in step (a); and (c) selecting at least one of the transformed cell clone(s) characterized in step (b) and further characterizing said at least one selected transformed cell clone.

In particular embodiments, the attenuated strain of *Salmonella* is of the species *Salmonella enterica*, more particularly of *Salmonella typhi*, most particularly of *Salmonella typhi* Ty21a.

In particular embodiments, the at least one expression cassette is a eukaryotic expression cassette.

In particular embodiments, said antigen is selected from the group consisting of a tumor antigen and a tumor stroma antigen, particularly selected from the group consisting of a human tumor antigen and a human tumor stroma antigen, more particularly selected from the group consisting of a human wild type tumor antigen, a protein that shares at least 80% sequence identity with a human wild type tumor antigen, a human wild type tumor stroma antigen and a protein that shares at least 80% sequence identity with a human wild type tumor stroma antigen. In a preferred embodiment, the antigen is a tumor antigen, more preferably a neoantigen.

In particular embodiments, said at least one DNA molecule comprises the kanamycin antibiotic resistance gene, the pMB1 ori, and a eukaryotic expression cassette encoding said antigen under the control of a CMV promoter, particularly wherein said DNA molecule is a DNA plasmid, more particularly wherein the DNA plasmid comprises the nucleic acid sequence as found in SEQ ID NO 1.

In particular embodiments, said attenuated strain of *Salmonella* is transformed by electroporation with said at least one DNA molecule comprising at least one expression cassette encoding at least one antigen or at least one fragment thereof in step (a).

In particular embodiments, step (b) comprises at least one of the following substeps (bi) through (biv): (bi) assessing the cell growth of at least one transformed cell clone obtained in step (a) over time; (bii) assessing the stability of the at least one DNA molecule comprising at least one expression cassette encoding at least one antigen or at least one fragment thereof in the at least one transformed cell clone obtained in step (a); (biii) isolating the at least one DNA molecule comprising at least one expression cassette encoding at least one antigen or at least one fragment thereof from at least one transformed cell clone obtained in step (a) and characterizing the at least one isolated DNA molecule by restriction analysis and/or sequencing; (biv) isolating the at least one DNA molecule comprising at least one expression cassette encoding at least one antigen or at least one fragment thereof from at least one transformed cell clone obtained in step (a), transfecting the at least one isolated DNA molecule into at least one eukaryotic cell and assessing the expression of the at least one antigen or the at least one fragment thereof in said at least one eukaryotic cell.

In particular embodiments, step (b) comprises one, two, three, or all four of said substeps (bi), (bii), (biii) and (biv).

In particular embodiments, step (c) comprises at least one of the following substeps (ci) through (cvi): (ci) assessing the number of viable cells per ml cell suspension of the at least one transformed cell clone selected in step (c); (cii) assessing the stability of the at least one DNA molecule comprising at least one expression cassette encoding at least one antigen or at least one fragment thereof in the at least one transformed cell clone selected in step (c); (ciii) isolating the at least one DNA molecule comprising at least one expression cassette encoding at least one antigen or at least one fragment thereof from the at least one transformed cell clone selected in step (c) and characterizing the at least one isolated DNA molecule by restriction analysis and/or sequencing; (civ) isolating the at least one DNA molecule comprising at least one expression cassette encoding at least one antigen or at least one fragment thereof from the at least one transformed cell clone selected in step (c), transfecting the at least one isolated DNA molecule into at least one eukaryotic cell and assessing the expression of the at least one antigen or the at least one fragment thereof in said at least one eukaryotic cell; (cv) testing for the presence of bacterial, fungal and/or viral contaminants in at the least one transformed cell clone selected in step (c); (cvi) verifying the bacterial strain identity of the at least one transformed cell clone selected in step (c).

In particular embodiments, step (c) comprises one, two, three, four, five, or all six of said substeps (ci), (cii), (ciii), (civ), (cv) and (cvi).

In particular embodiments, the presence of bacterial and/or fungal contaminants is tested in step (cv) by growing the at least one transformed cell clone selected in step (c) in or on at least one suitable selective medium.

In particular embodiments, the bacterial strain identity is verified in step (cvi) by growing the at least one transformed cell clone selected in step (c) on bromothymol blue galactose agar and/or on Kligler iron agar and/or by assessing the presence of *Salmonella* O5 and/or O9-surface antigen(s).

In a second aspect, the present invention relates to a DNA vaccine obtainable by the method according to the present invention.

In a third aspect, the present invention relates to the DNA vaccine according to the present invention for use in cancer immunotherapy.

DETAILED DESCRIPTION OF THE INVENTION

The present invention may be understood more readily by reference to the following detailed description of the invention and the examples included therein.

In a first aspect, the present invention relates to a method for producing a DNA vaccine for cancer immunotherapy comprising at least steps of (a) transforming an attenuated strain of *Salmonella* with at least one DNA molecule comprising at least one expression cassette encoding at least one antigen or at least one fragment thereof; (b) characterizing at least one transformed cell clone obtained in step (a); and (c) selecting at least one of the transformed cell clone(s) characterized in step (b) and further characterizing said at least one selected transformed cell clone.

The method according to the present invention allows for the rapid and cost-effective production of *Salmonella*-based DNA vaccines. The entire process including the generation of the antigen encoding DNA molecule, the transformation into the *Salmonella* recipient strain, the characterization of candidate clones and the selection and further characterization of the final DNA vaccine to be administered to the patient, takes less than four weeks, particularly less than three weeks, and typically as few as 16 days. Patient-specific DNA vaccines may conveniently be produced by small batch manufacture, which allows for the simultaneous generation, cultivation and characterization of several transformed *Salmonella* clones in parallel. Stepwise cell clone characterization maximizes product quality and minimizes process duration. The production process is highly robust and yields a safe and well-characterized DNA vaccine.

In the context of the present invention, the term "vaccine" refers to an agent which is able to induce an immune response in a subject upon administration. A vaccine can preferably prevent, ameliorate or treat a disease. A vaccine in accordance with the present invention comprises an attenuated strain of *Salmonella*, preferably *S. typhi* Ty21a. The vaccine in accordance with the present invention further comprises at least one copy of a DNA molecule comprising at least one expression cassette, preferably a eukaryotic expression cassette, encoding at least one antigen or at least one fragment thereof, preferably selected from a human tumor antigen, a fragment of a human tumor antigen, a human tumor stroma antigen, and a fragment of a human tumor stroma antigen.

According to the invention, the attenuated *Salmonella* strain functions as the bacterial carrier of the DNA molecule comprising an expression cassette encoding at least one antigen or at least one fragment thereof for the delivery of said DNA molecule into a target cell. Such a delivery vector comprising a DNA molecule encoding a heterologous antigen, such as a tumor antigen, a tumor stroma antigen or a fragment thereof, is termed DNA vaccine.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

Live bacterial vectors produce their own immunomodulatory factors such as lipopolysaccharides (LPS) in situ which may constitute an advantage over other forms of administration such as microencapsulation. Moreover, the use of the natural route of entry proves to be of benefit since many bacteria, like *Salmonella*, egress from the gut lumen via the M cells of Peyer's patches and migrate eventually into the lymph nodes and spleen, thus allowing targeting of vaccines to inductive sites of the immune system. The vaccine strain of *Salmonella typhi*, Ty21a, has been demonstrated to-date to have an excellent safety profile. Upon exit from the gut lumen via the M cells, the bacteria are taken up by phagocytic cells, such as macrophages and dendritic cells. These cells are activated by the pathogen and start to differentiate, and probably migrate into the lymph nodes and spleen. Due to their attenuating mutations, bacteria of the S. typhi Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to antigen expression in the cytosol of the phagocytic cells. Specific cytotoxic T cells against the encoded antigen are induced by the activated antigen presenting cells.

There is no data available to-date indicating that S. typhi Ty21a is able to enter the bloodstream systemically. The live attenuated Salmonella typhi Ty21a vaccine strain thus allows specific targeting of the immune system while exhibiting an excellent safety profile.

Attenuated derivatives of Salmonella enterica are attractive as vehicles for the delivery of heterologous antigens to the mammalian immune system because S. enterica strains can potentially be delivered via mucosal routes of immunization, i.e. orally or nasally, which offers advantages of simplicity and safety compared to parenteral administration. Furthermore, Salmonella strains elicit strong humoral and cellular immune responses at the level of both systemic and mucosal compartments.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology. Administration of about $10^{11}$ CFU of the attenuated strain of Salmonella according to the present invention preferably causes Salmonellosis in less than 5%, more preferably less than 1%, most preferably less than 1‰ of subjects.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

The at least one DNA molecule comprising at least one expression cassette encoding at least one antigen or at least one fragment thereof is suitably a recombinant DNA molecule, i.e. an engineered DNA construct, preferably composed of DNA pieces of different origin. The DNA molecule can be a linear nucleic acid, or preferably, a circular DNA plasmid generated by introducing an open reading frame encoding at least one antigen or at least one fragment thereof into an expression vector plasmid.

In the context of the present invention, the term "expression cassette" refers to a nucleic acid unit comprising at least one antigen encoding gene or at least one fragment thereof under the control of regulatory sequences controlling its expression. The expression cassette comprised in the attenuated strain of Salmonella can preferably mediate transcription of the included open reading frame encoding at least one antigen or at least one fragment thereof in a target cell. Expression cassettes typically comprise a promoter, at least one open reading frame and a transcription termination signal.

In the context of the present invention, the term "transformed cell clone" refers to a cell population derived from a single cell colony obtained after Salmonella recipient strain transformation. Since the cells are derived from a single colony picked from a selection medium agar plate, it is assumed that all the cells derive from one single transformed Salmonella cell. However, the cell population derived from such a single colony obtained after transformation may comprise contaminants such as other bacteria, fungi or viruses.

In particular embodiments, the attenuated strain of Salmonella is of the species Salmonella enterica, more particularly of Salmonella typhi, most particularly of Salmonella typhi Ty21a.

In particular embodiments, the attenuated strain of Salmonella is of the species Salmonella enterica. In particular embodiments, the attenuated strain of Salmonella is Salmonella typhi Ty21a. The attenuated S. typhi Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries. The Marketing Authorization number of Typhoral L® is PL 15747/0001 dated 16 Dec. 1996. One dose of vaccine contains at least $2 \times 10^9$ viable S. typhi Ty21a colony forming units and at least $5 \times 10^9$ non-viable S. typhi Ty21a cells.

One of the biochemical properties of the Salmonella typhi Ty21a bacterial strain is its inability to metabolize galactose. The attenuated bacterial strain is also not able to reduce sulfate to sulfide which differentiates it from the wild type Salmonella typhi Ty2 strain. With regard to its serological characteristics, the Salmonella typhi Ty21a strain contains the 09-antigen which is a polysaccharide of the outer membrane of the bacteria and lacks the 05-antigen which is in turn a characteristic component of Salmonella typhimurium. This serological characteristic supports the rationale for including the respective test in a panel of identity tests for batch release.

In particular embodiments, the S. typhi Ty21a recipient strain, i.e. the S. typhi Ty21a cells to be transformed with the at least one DNA molecule comprising at least one expression cassette encoding at least one antigen or at least one fragment thereof, can be generated based on commercially available Typhoral L® capsules without biochemical modification. After overnight culture on agar plates single colonies may be isolated and grown in 100 ml TSB culture medium overnight at 37° C. The cultures may then be formulated with 15% sterile glycerol, aliquoted (1 ml), labelled, frozen, and stored at −75° C.±5° C. as Master Cell Bank, pending use.

In particular embodiments, the bacterial strain identity of the thus obtained S. typhi Ty21a recipient strain may be verified by growing the strain on bromothymol blue galactose agar and/or on Kligler iron agar. The characteristics of

*S. typhi* Ty21a colonies on such agar plates used as Master Cell Bank are described in Table 1.

In particular embodiments, the detection of bacteriophages may be performed by plating in soft-agar overlays containing an appropriate host and either the sample to be tested or a control suspension of phages. To improve the sensitivity of the assay a preceding enrichment step may be included. In this optional step the samples are incubated for 4 h with appropriate host cells. Subsequently, one sample of each of these enrichment cultures is plated.

TABLE 1

Characterization Testing of the *Salmonella Typhi* Ty 21a Isolates for Use as Master Cell Bank

| Test Parameter | Test Method | Ty21a colony characteristics |
|---|---|---|
| Identity | BTB-Gal Agar | green to yellowish colonies without discoloration of the medium |
| | Kligler Iron Agar | yellow coloration of the medium, no or only little gas formation |
| | Genome Identity - Sequencing | Corresponds to reference sequence (Ty21a) |
| Potency | Growth Kinetics - pH in Culture Medium | Corresponds to *S. Typhi* Ty21a |
| Purity | Bacteriophage Testing (SOP 97) | No phages detectable |

In particular embodiments, the viable cell number of the prepared recipient strain aliquots is from $10^7$ to $10^{11}$, more particularly from $10^8$ to $10^{10}$, most particularly about $10^9$ CFU/ml.

In particular embodiments, the at least one expression cassette is a eukaryotic expression cassette. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and result in cell death, overattenuation or loss of expression of the heterologous antigen. Using a eukaryotic expression cassette that is not expressed in the bacterial vector but only in the target cell may overcome this toxicity problem and the protein expressed may exhibit a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated strain of *Salmonella* of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the DNA molecule comprised by the attenuated strain of *Salmonella* of the present invention comprises the BGH polyadenylation site.

In addition to the regulatory elements required for expression of the heterologous antigen encoding gene, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, said antigen is selected from the group consisting of a tumor antigen and a tumor stroma antigen. Particularly, said antigen is selected from the group consisting of a human tumor antigen and a human tumor stroma antigen, more particularly from the group consisting of a human wild type tumor antigen, a protein that shares at least 80% sequence identity with a human wild type tumor antigen, a human wild type tumor stroma antigen and a protein that shares at least 80% sequence identity with a human wild type tumor stroma antigen. In particular embodiments, the at least one expression cassette encodes at least one fragment of at least one antigen, particularly at least one fragment of a tumor antigen and/or at least one fragment of a tumor stroma antigen, more particularly at least one fragment of at least one human tumor antigen and/or at least one human tumor stroma antigen, including fragments of proteins that share at least 80% sequence identity with a human wild type tumor antigen or a human wild type tumor stroma antigen. In particular embodiments, the at least one fragment of the at least one antigen comprises at least 5 consecutive amino acids of the reference antigen, more particularly at least 6, 7, 8, 9, 10, 15, 20, 25, amino acids of the reference antigen. In particular embodiments, the at least one antigen fragment comprises at least one epitope, more particularly at least 2, 3, 4, 5, 6, 7, 8, 9, 10, 15, 20, 30, 40, 50, 60, 80 or 100 epitopes of the reference antigen. In particular embodiments, the at least one antigen fragment comprises from 1 to 100, or from 1 to 75, or from 1 to 50, or from 1 to 25 epitopes, in particular from 1 to 10 epitopes, more particularly from 1 to 5 epitopes. In the context of the present invention, the term "epitope" refers to a part of a given antigen that participates in the specific binding between the antigen and an antigen binding molecule such as an antibody. An epitope may be continuous, i.e. formed by adjacent structural elements present in the antigen, or discontinuous, i.e. formed by structural elements that are at different positions in the primary sequence of the antigen, such as in the amino acid sequence of the antigen protein, but in close proximity in the three-dimensional structure, which the antigen adopts, such as in the bodily fluid. According to the teaching of the present invention, the at least one fragment of the antigen may comprise any number of amino acids of the reference antigen, as long as the fragment of the antigen is immunogenic. Preferably, the immunogenicity of the at least one antigen fragment is reduced by less than 50%, less than 40%, less than 30%, less than 20%, less than 10%, less than 5% or less than 1% compared to the reference antigen, as measured by ELISA or as measured by ELISpot.

In the context of the present invention, the term "tumor antigen" refers to an antigen that is expressed in tumor cells. Typically, such tumor antigens are preferentially expressed by tumor cells, i.e. they are not or only weakly expressed by non-malignant cells or are only expressed in certain non-malignant tissues. In contrast, tumor stroma antigens are expressed by the tumor stroma, for instance by the tumor vasculature. One example of such a tumor stroma antigen is VEGFR-2, which is highly expressed by the tumor vasculature. In particular embodiments, the encoded VEGFR-2 antigen has the amino acid sequence as found in SEQ ID NO 2 or shares at least about 80% sequence identity therewith. Another example of a tumor stroma antigen is human fibroblast activation protein (FAP). The tumor antigens may be selected from known tumor antigens that are commonly expressed in a large proportion of cancers of a given type or of cancers in general. The term "tumor antigen" also comprises neoantigens, i.e. tumor-specific antigens that arise as a consequence of tumor-specific mutations. These neoantigens may either be patient specific or may occur in a number of cancer patients. In particular embodiments, the tumor antigen may be selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith and CMV pp65 having the amino acid sequence as found in SEQ ID NO 8 and a protein that shares at least about 80% sequence identity therewith.

In particular embodiments, human VEGFR-2 has the amino acid sequence as found in SEQ ID NO 2, human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found-in SEQ ID NO 5, and CMV pp65 has the amino acid sequence as found in SEQ ID NO 6, SEQ ID NO 7 or SEQ ID NO 8.

The tumor antigen and/or the tumor stroma antigen may also be a patient specific tumor antigen and/or tumor stroma antigen, i.e. an antigen that was shown to be expressed by tumor cells or the tumor stroma of one specific patient. Patient specific tumor antigens and/or tumor stroma antigens may be identified by assessing the expression profile of a patient's tumor and/or tumor stroma either on mRNA or on protein level. Alternatively, pre-existing T-cell immune responses to tumor antigens and/or tumor stroma antigens of a patient may be assessed. After having identified a patient specific tumor antigen and/or tumor stroma antigen, the method according to the present invention allows for the rapid manufacture of a safe, well characterized, patient-specific DNA vaccine suitable for cancer immunotherapy. Typically, the entire manufacturing process including the generation of the antigen encoding expression plasmid, the transformation into the *Salmonella* recipient strain, the characterization of candidate clones and the selection and further characterization of the final DNA vaccine to be administered to the patient, takes less than four weeks, particularly less than three weeks, and typically as few as 16 days.

In the context of the present invention, the term "protein that shares at least about 80% sequence identity with a tumor antigen or a tumor stroma antigen of a given sequence" refers to a protein that differs in the amino acid sequence and/or the nucleic acid sequence encoding the amino acid sequence of the given reference protein. The protein may be of natural origin, e.g. a homolog of the tumor antigen or the tumor stroma antigen, or an engineered protein. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

The protein that shares at least about 80% sequence identity with a tumor antigen or a tumor stroma antigen of a given amino acid sequence may contain one or more mutations comprising an addition, a deletion and/or a substitution of one or more amino acids, as compared to the given reference amino acid sequence. According to the teaching of the present invention, said deleted, added and/or substituted amino acids may be consecutive amino acids or may be interspersed over the length of the amino acid sequence of the protein that shares at least about 80% sequence identity a given tumor antigen or a tumor stroma antigen. According to the teaching of the present invention, any number of amino acids may be added, deleted, and/or substitutes, as long as the sequence identity with the reference tumor antigen or tumor stroma antigen is at least about 80% and the mutated tumor antigen or tumor stroma antigen protein is immunogenic. Preferably, the immunogenicity of the tumor antigen or the tumor stroma antigen that shares at least about 80% sequence identity with a reference tumor antigen or tumor stroma antigen of a given amino acid sequence is reduced by less than 50%, less than 40%, less than 30%, less than 20%, less than 10%, less than 5% or less than 1% compared to the reference tumor antigen or tumor stroma antigen of the given amino acid sequence, as measured by ELISA or as measured by ELISpot. Methods for designing and constructing protein homologues and for testing such homologues for their immunogenic potential are well known to anyone of ordinary skill in the art. In particular embodiments, the sequence identity with a given tumor antigen or tumor stroma antigen of a given amino acid sequence is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with a tumor antigen or a tumor stroma antigen of a given amino acid sequence may differ to a larger extent due to the degeneracy of the genetic code.

In particular embodiments, said at least one DNA molecule comprises the kanamycin antibiotic resistance gene as a selection marker, the pMB1 ori, and a eukaryotic expression cassette encoding said antigen under the control of a CMV promoter, particularly wherein said DNA molecule is a DNA plasmid, more particularly wherein the DNA plasmid comprises the nucleic acid sequence as found in SEQ ID NO 1.

In particular embodiments, the DNA molecule is a recombinant DNA molecule derived from commercially available pVAX1™ expression plasmid (Invitrogen, San Diego, Calif.). pVAX1 is a plasmid vector for expression of proteins in eukaryotic cells which was specifically designed for use in the development of DNA vaccines by modifying the vector pcDNA3.1. Sequences not necessary for replication in bacteria or for expression of recombinant protein in mammalian cells were removed to limit DNA sequences with possible homology to the human genome and to minimize the possibility of chromosomal integration. Furthermore, the ampicillin resistance gene in pcDNA3.1 was replaced by the kanamycin resistance gene because aminoglycoside antibiotics are less likely to elicit allergic responses in humans.

The pVAX1™ vector contains the following elements: the human cytomegalovirus immediate-early (CMV) promoter for high-level expression in mammalian cells, the bovine growth hormone (BGH) polyadenylation signal for efficient transcription termination and polyadenylation of mRNA, and the kanamycin resistance gene as a selection marker.

In addition pVAX1™ contains a multiple cloning site for insertion of the gene of interest as well as a T7 promoter/priming site upstream and a BGH reverse priming site downstream of the multiple cloning site to allow sequencing and in vitro translation of the clones gene.

The commercially available pVAX1™ expression vector was further modified by replacing the high copy pUC origin of replication by the low copy pMB1 origin of replication of pBR322. The low copy modification was made in order to reduce the metabolic burden and to render the construct more stable. The generated expression vector backbone was designated pVAX10. Importantly, data obtained from transfection experiments using the 293T human cell line demonstrated that the kanamycin resistance gene encoded on pVAX10 is not translated in human cells. The expression system thus complies with regulatory requirements.

In particular embodiments, the at least one DNA molecule comprising at least one expression cassette encoding at least one antigen or at least one fragment thereof to be transformed into the attenuated *Salmonella* recipient strain is generated by cloning the at least one antigen cDNA or the at least one fragment thereof into the pVAX10 vector backbone. The vector backbone may be isolated from plasmid pVAX10.VR2-1, containing the cDNA for human VEFGR-2 cloned into the pVAX10 vector backbone. The VEGFR-2 cDNA can be excised from pVAX10.VR2-1 and the pVAX10 vector backbone may then be isolated by agarose gel electrophoresis.

In particular embodiments, synthesis of the cDNA insert is performed by double strand in vitro gene synthesis. The steps of the synthesis process are presented in FIG. 3.

In particular embodiments, said attenuated strain of *Salmonella* is transformed by electroporation with said at least one DNA molecule comprising at least one expression cassette encoding at least one antigen or at least one fragment thereof in step (a).

In particular embodiments, the *S. typhi* Ty21a strain Master Cell Bank (MCB) based on commercially available Typhoral L® capsules is used as starting strain for the preparation of the batch production clone. In order to obtain competent cells for electroporation the S. *Typhi* Ty21a MCB is resuspended in 500 ml of ice cold $H_2O$ and centrifuged. After two further washes in ice cold water/10% glycerol the pellet is resuspended in 2 ml of 10% glycerol (animal free), aliquoted (50 µl) and frozen on dry ice. Competent cell batches are stored for maximum 4 weeks after at <−70° C. which a new competent cell batch is freshly produced. For transformation one aliquot of competent cells is thawed and electroporated in the presence of 3-5 µl of plasmid DNA encoding the desired antigen. Following a brief incubation period in 1 ml of LB (ACF) medium at 37° C., the cell suspension is streaked on LB (ACF) agar plates containing kanamycin (25 and 50 µg/mL). The plates are incubated at 37° C. overnight.

At least one single colony, typically from 1 to 10 colonies, particularly from 2 to 5 colonies are further tested to allow for the selection of at least one transformed cell clone for preparation of the batch production clone. Conveniently, three single colonies are used to inoculate 3 ml of LB medium (ACF soy peptone) containing kanamycin (50 µg/ml). Cultures are incubated at 37° C. overnight. Plasmid DNA is isolated and the selected clones are expanded in LB medium containing 50 µg/ml kanamycin. Cultures are mixed with 10% (v/v) glycerol, aliquoted (1 ml) and stored frozen at −70° C.

In particular embodiments, at least one of the following analytical parameters is evaluated in step (b) for selection of the batch production clone: growth kinetics over time upon culturing in selective medium determined by OD600, pH and CFU; plasmid stability after cryo-conservation (% PS); plasmid DNA extraction and confirmation of identity by plasmid restriction analysis; and determination of antigen expression efficacy after transient transfection of the plasmid DNA into an eukaryotic cell line. In particular embodiments, the batch production clone is then used to prepare drug substance (DS), which is then further characterized in step (c) to establish the final drug product (DP) to be administered to a patient.

Thus, in particular embodiments, step (b) comprises at least one of the following substeps (bi) through (biv): (bi) assessing the cell growth of at least one transformed cell clone obtained in step (a) over time; (bii) assessing the stability of the at least one DNA molecule comprising at least one expression cassette encoding at least one antigen or at least one fragment thereof in the at least one transformed cell clone obtained in step (a); (biii) isolating the at least one DNA molecule comprising at least one expression cassette encoding at least one antigen or at least one fragment thereof from at least one transformed cell clone obtained in step (a) and characterizing the at least one isolated DNA molecule by restriction analysis and/or sequencing; (biv) isolating the at least one DNA molecule comprising at least one expression cassette encoding at least one antigen or at least one fragment thereof from at least one transformed cell clone obtained in step (a), transfecting the at least one isolated DNA molecule into at least one eukaryotic cell and assessing the expression of the at least one antigen or the at least one fragment thereof in said at least one eukaryotic cell.

Particularly, step (bii) may be carried out after freezing and subsequent thawing of said at least one transformed cell clone.

Particularly, step (biv) may be carried out by transfecting HEK293T cells with plasmid DNA isolated from the single colonies obtained after *Salmonella* recipient strain transformation and performing Western blot analysis of the cell extracts using an appropriate antibody for the encoded antigen.

In particular embodiments, step (b) comprises one, two, three, or all four of said substeps (bi), (bii), (biii) and (biv).

In particular embodiments, step (b) comprises only substeps (bi), (bii) and (biii).

After consideration of the data obtained from growth characteristics, plasmid stability, plasmid identity and/or protein expression studies, at least one transformed cell clone is selected as the batch production clone. In particular embodiments, the batch production clone is then used to prepare the drug substance (DS), which is then further characterized in step (c) to establish the final drug product (DP) to be administered to a patient.

An outline of the manufacture of the Drug Product is depicted in FIGS. 1 and 2.

The manufacture of the Drug Substance (DS) may conveniently be carried out as described in the following: The DS is typically manufactured in compliance with GMP requirements. At least one batch production clone is transferred to three 50 ml flasks containing TSB medium plus 25 µg/ml kanamycin (Preculture 1). Colonies are grown to a maximum $OD_{600}$ of <1.0 for 9 h±1 h at 30° C. Agitation of each flask is set at 120 rpm. The flask with the highest OD value is selected for further cultivation. A volume of 50 ml of the Preculture 1 is transferred to a flask containing 1000 ml TSB medium plus 25 µg/ml kanamycin (main culture). After incubation at 30° C. for 9 h±1 h, with agitation set at 180 rpm, the bacteria are grown to a target $OD_{600}$ between 0.9 and 1.5. Once the fermentation is completed, glycerol is added to the culture to a final concentration of 15% (w/w). The suspension is mixed and then aliquoted (1 ml) into 2 ml cryovials. The vials are labelled and frozen immediately at −75° C.±5° C. for storage. It is to be understood that the described process workflow only describes one possible way to manufacture the Drug Substance. Of course, the process parameters, for example the culture volumes may be varied.

The Drug Substance is then further tested to dilute it to the final drug product concentration. Release specifications have been established for both, Drug Substance and Drug Product. At least one of the properties summarized in Table 2 and Table 3 are tested.

TABLE 2

Release Specifications for Drug Substance

| Test | Test method | Acceptance criterion |
|---|---|---|
| Potency | Viable Cell Count | ≥$10^7$ CFU/mL |
|  | Plasmid Stability | ≥66% |
| Purity | Microbial Impurity EP 2.6.12/2.6.13 (SOP M 073) | TAMC ≤$10^2$ CFU/mL<br>TYMC ≤20 CFU/mL<br>Absence of the species in 1 mL:<br>P. aeruginosa,<br>S. aureus, E. coli,<br>Clostridium sp.<br>and other Salmonella |
| Identity | Bromothymol blue galactose agar | Colony growth in the presence of 1.25% galactose, light blue transparent and/or green to yellowish colonies without colour change of the medium |
|  | Kligler Iron-Agar | Yellow coloring of the medium, no blackening, lack of $H_2S$ formation |
|  | Serological Test | O9-positive<br>O5-negative |
| Plasmid Identity | Restriction analysis | Determination of complete DNA-fragments after restriction enzyme digestion with different DNA-nucleases corresponds to theoretical fragment lengths (±10%). |
|  | DNA-Sequencing (ATM-0274) | Corresponds to reference sequence |

TABLE 3

Release Specifications for Drug Product

| Test | Test method | Acceptance criterion |
|---|---|---|
| Potency | Viable Cell Count | ≥$10^7$ CFU/mL |
|  | Plasmid Stability | ≥66% |
| Identity | Bromothymol blue galactose agar | Colony growth in the presence of 1.25% galactose, light blue transparent and/or green to yellowish colonies without colour change of the medium |
|  | Kligler Iron-Agar | Yellow coloring of the medium, no blackening, lack of $H_2S$ formation |
|  | Serological Test | O9-positive<br>O5-negative |

Thus, in particular embodiments, step (c) comprises at least one of the following substeps (ci) through (cvi): (ci) assessing the number of viable cells per ml cell suspension of the at least one transformed cell clone selected in step (c); (cii) assessing the stability of the at least one DNA molecule comprising at least one expression cassette encoding at least one antigen or at least one fragment thereof in the at least one transformed cell clone selected in step (c); (ciii) isolating the at least one DNA molecule comprising at least one expression cassette encoding at least one antigen or at least one fragment thereof from the at least one transformed cell clone selected in step (c) and characterizing the at least one isolated DNA molecule by restriction analysis and/or sequencing; (civ) isolating the at least one DNA molecule comprising at least one expression cassette encoding at least one antigen or at least one fragment thereof from the at least one transformed cell clone selected in step (c), transfecting the at least one isolated DNA molecule into at least one eukaryotic cell and assessing the expression of the at least one antigen or the at least one fragment thereof in said at least one eukaryotic cell; (cv) testing for the presence of bacterial, fungal and/or viral contaminants in at the least one transformed cell clone selected in step (c); (cvi) verifying the bacterial strain identity of the at least one transformed cell clone selected in step (c).

In particular embodiments, substep (cii) is carried out after freezing and subsequent thawing of said at least one transformed cell clone.

In particular embodiments, step (c) comprises one, two, three, four, five, or all six of said substeps (ci), (cii), (ciii), (civ), (cv) and (cvi).

In particular embodiments, step (c) comprises substeps (ci), (cii), (ciii), (cv) and (cvi).

Particularly, the number of viable cells may be determined by plating serial dilutions on agar plates. Conveniently, serial dilutions of the bacterial suspension down to a dilution factor of $10^{-8}$ are prepared and plated onto the agar plates. After appropriate incubation, colonies are counted. Counting should start, when colonies are clearly visible, but not too large.

Plasmid stability may be determined based on the kanamycin resistance of plasmid containing *Salmonella* bacteria. Growth of bacterial cells on TSB containing kanamycin indicates the presence of plasmids coding for the kanamycin resistance gene. Comparing the CFUs of the same sample plated on TSB plates with and without kanamycin allows the determination of the fraction of bacteria that carry the plasmid. Particularly, serial dilutions of the bacterial suspension are prepared and plated onto TSB plates optionally containing the antibiotic kanamycin. After appropriate incubation colonies are counted. Counting should start, when colonies are clearly visible, but not too large. The plasmid stability is calculated by comparing colony forming units on TSB with and without kanamycin as follows: PST=(CFU with kanamycin/CFU without kanamycin)×100.

Plasmid identity may be defined by the comparison of the size pattern of digested plasmid isolated from the vaccine strain with size markers. Particularly, the recombinant plasmid is isolated from the carrier and digested with at least one, typically at least two different digestion enzymes/combinations in separate reactions for an appropriate time. The reaction is stopped and analyzed on an agarose gel.

The identity of the genetic construct may further be determined through classical DNA sequencing of the plasmid. The sequence of the entire plasmid is determined by sequencing and is aligned to the original sequence of the plasmid. Particularly, the plasmid is prepared from *Salmonella* and quantified. It is then retransformed in *E. coli*, isolated, quantified and used for the sequencing reaction.

Expression of the at least one antigen or the at least one fragment thereof in eukaryotic cells may be verified by expression analysis after plasmid transfection into a eukaryotic cell line and Western blotting. Particularly, the recombinant construct is isolated from the carrier strain and used for transfection of a suitable eukaryotic permanent cell line. Due to the presence of a eukaryotic promoter, the encoding sequence is expressed. After suitable incubation, protein isolation and subsequent Western blotting, the presence of the recombinant protein is demonstrated and compared on a semi-quantitative basis with the reference material.

In particular embodiments, the presence of bacterial and/or fungal contaminants is tested in step (cv) by growing the at least one transformed cell clone selected in step (c) in or on at least one suitable selective medium. Particularly, in order to determine counts of total aerobic bacteria, molds and fungi and confirm the absence of the specific germs *Escherichia coli, Salmonella* sp., *Pseudomonas aeruginosa, Staphylococcus aureus*, and *Clostridium* sp. the sample may be tested in accordance with the monograph of the European Pharmacopoeia 04/2009:1055<Thyphoid Vaccine (Live, oral, strain Ty 21a)> using suitable selective media. Particularly, the test is conducted according to the European Pharmacopoeia Ph. Eur. monographs 2.6.12 and 2.16.13.

In particular embodiments, the bacterial strain identity is verified in step (cvi) by growing the at least one transformed cell clone selected in step (c) on bromothymol blue galactose (BTB-Gal) agar and/or on Kligler iron agar (KIA) and/or by assessing the presence of *Salmonella* 05 and/or 09-surface antigen(s).

The biochemical identity test relies on two selective media detecting biochemical properties (mainly galactose fermentation and sulfide production) of the microorganisms. In contrast to other *Salmonella* species, the attenuated vaccine strain Ty21a is not able to metabolize galactose. Growth on BTB-Gal-agar results in green to yellowish colonies without changing the colour of the medium. In contrast, cultivation of wild type *Salmonella* on BTB-Gal results in a strong yellow coloration of the media due to acid production during metabolization of galactose and subsequent colour change of the pH indicator (bromthymol blue). S. *Typhi* Ty21a can build morphological distinct sub-clones when growing on BTB-Gal. This additional type is characterized by decelerated growth of small, grey colonies upon and in-between the characteristic *Salmonella* colonies.

Kligler iron agar is used to differentiate members of the Enterobacteria. The features of this medium are based on the capability of the Enterobacteria to metabolize dextrose and lactose and to liberate sulphides. The Ty21a vaccine strain is able to metabolize dextrose indicated by a colour change of the pH indicator from red to yellow. However, strain S. *Typhi* Ty21a is not able to reduce sulfate to sulfide, while other Salmonellae blacken the colour of the media during hydrogen sulfide production and liberate gas which result in bubble formation within the agar. Growth of S. *Typhi* Ty21a can result in gas production, but is not typical for this strain. Organisms incapable of metabolizing either sugar like *P. aeruginosa*, do not alter the colour of the medium.

Particularly, bacterial strain identity may be biochemically verified as described in the following. A loop of the completely thawed suspension is transferred to the BTB-Gal-agar plates applying an appropriate streaking method to obtain single colonies. The inoculation of the control organism *P. aeruginosa* (ATCC 9027) and *S. typhimurium* (Moskau) is performed by transferring a bead of a Microbank® (storage system for microbial cultures) and subsequent streaking on the agar plate. For inoculation of KIA a loop (bead) of the same vial is first streaked onto the surface of the slant and then infeeded into the butt. The media are incubated for 48 h at 37° C.

The different serovars of the genus *Salmonella* can be differentiated using the appropriate polyclonal antisera or monoclonal antibodies. The attenuated recombinant S. *Typhi* Ty21a strain contains the 09-antigen which is a polysaccharide of the outer membrane. S. *Typhi* carries 09 but lacks 05 which is in turn characteristic of *S. typhimurium*. By combination of tests for the 05 and 09 antigens, the S. *Typhi* Ty21a strain can be well discriminated from other bacteria and particularly from wild type *Salmonella* species. Particularly, serotyping may be performed as described in the following. A drop of antiserum (05 or 09) is transferred to a chamber slide. A loop of colony containing material is taken from the lower (wet) side of the KIA and placed next to the antiserum. The solutions are mixed with the loop. The resulting suspension should be slightly turbid. The suspension is distributed by wiping of the chamber slides several times. The reactions are evaluated after 2 min against a black background.

In a second aspect, the present invention relates to a DNA vaccine obtainable by the method according to the present invention.

In a third aspect, the present invention relates to the DNA vaccine according to the present invention for use in cancer immunotherapy.

In particular embodiments, cancer immunotherapy comprises personalized cancer immunotherapy.

In particular embodiments, cancer immunotherapy further comprises administration of one or more further attenuated strain(s) of *Salmonella* comprising at least one copy of a DNA molecule comprising an expression cassette encoding a tumor antigen and/or a tumor stroma antigen, particularly wherein said one or more further attenuated strain(s) of *Salmonella* is/are *Salmonella typhi* Ty21a comprising a eukaryotic expression cassette, more particularly wherein said one or more further attenuated strain(s) of *Salmonella* comprise(s) an attenuated strain of *Salmonella* encoding human VEGFR-2 and/or human Wilms' Tumor Protein (WT1) and/or human Mesothelin (MSLN) and/or human CEA and/or pp65 of human CMV.

Combining two different tumor antigen and/or tumor stroma antigen targeting DNA vaccines may have synergistic antitumor effects. In particular, simultaneous targeting of different tumor antigens/tumor stroma antigens may minimize the risk of tumor escape. Combining a tumor antigen targeting DNA vaccine with a tumor stroma antigen targeting DNA vaccine may prove especially effective, since tumor cells and the tumor stroma are attacked at the same time.

In particular embodiments, the attenuated strain of *Salmonella* is co-administered with said one or more further attenuated strain(s) of *Salmonella*.

In the context of the present invention, the term "co-administration" or "co-administer" means administration of two different attenuated strains of *Salmonella* within three consecutive days, more particularly within two consecutive days, more particularly on the same day, more particularly within 12 hours. Most particularly, in the context of the present invention, the term "co-administration" refers to simultaneous administration of two different attenuated strains of *Salmonella*.

In particular embodiments, a patient may first receive a Ty21a-based DNA vaccine targeting a tumor antigen or a tumor stroma antigen that is commonly overexpressed in the type of cancer the patient is suffering from. During this "first line" treatment, a patient-specific tumor antigen and/or tumor stroma antigen may be identified. For this purpose the patient's tumor and/or stromal antigen expression pattern and/or the patient's pre-existing T-cell immune responses against tumor and/or stromal antigens may be assessed in a first step for example by companion diagnostics targeting the patient's specific tumor and/or stromal antigen pattern. The method according to the present invention then allows for the rapid establishment of a safe and well characterized patient-specific (personalized) DNA vaccine, which may be used as "second line", or main treatment, only weeks after the identification of a patient-specific tumor antigen and/or tumor stroma antigen.

In particular embodiments, cancer immunotherapy is accompanied by chemotherapy, radiotherapy or biological cancer therapy. For cure of cancer, complete eradication of cancer stem cells may be essential. For maximal efficacy, a combination of different therapy approaches may be beneficial.

In the context of the present invention, the term "biological cancer therapy" refers to cancer therapy involving the use of living organisms, substances derived from living organisms, or laboratory-produced versions of such substances. Some biological therapies for cancer aim at stimulating the body's immune system to act against cancer cells (so called biological cancer immunotherapy). Biological cancer therapy approaches include the delivery of tumor antigens, delivery of therapeutic antibodies as drugs, administration of immunostimulatory cytokines and administration of immune cells. Therapeutic antibodies include antibodies targeting tumor antigens or tumor stroma antigens as well as antibodies functioning as checkpoint inhibitors, such as, but not limited to anti-PD-1, anti-PD-L1 and anti-CTLA4.

Chemotherapeutic agents that may be used in combination with the attenuated strain of *Salmonella* of the present invention may be, for example: gemcitabine, amifostine (ethyol), cabazitaxel, cisplatin, dacarbazine (DTIC), dactinomycin, docetaxel, mechlorethamine, streptozocin, cyclophosphamide, carmustine (BCNU), lomustine (CCNU), nimustine (ACNU), doxorubicin (adriamycin), doxorubicin lipo (doxil), folinic acid, gemcitabine (gemzar), daunorubicin, daunorubicin lipo (daunoxome), procarbazine, ketoconazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, temozolomide, teniposide, testolactone, thioguanine, thiotepa, uracil mustard, vinorelbine, chlorambucil and combinations thereof.

It may be also favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived autoaggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In particular embodiments, the attenuated strain of *Salmonella* is administered before or during the chemotherapy or the radiotherapy treatment cycle or before or during biological cancer therapy, or before and during the chemotherapy or the radiotherapy treatment cycle or the biological cancer therapy. This approach may have the advantage that chemotherapy or radiotherapy can be performed under conditions of enhanced cancer immunity.

In particular embodiments, the attenuated strain of *Salmonella* is administered after the chemotherapy or the radiotherapy treatment cycle or after biological cancer therapy.

In particular embodiments, the attenuated strain of *Salmonella* is administered orally. Oral administration is simpler, safer and more comfortable than parenteral administration. In contrast, intravenous administration of live bacterial vaccines initially causes a bacteremia associated with safety risks of the sepsis-type and thus calls for careful observation and monitoring of clinical symptoms such as cytokine release. Oral administration of the attenuated strain of the present invention may at least in part overcome the described risks. However, it has to be noted that the attenuated strain of Salmonella of the present invention may also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

The attenuated strain of Salmonella of the present invention may be provided in the form of a solution, a suspension, lyophilisate, or any other suitable form. It may be provided in combination with pharmaceutically acceptable carriers, diluents, and/or excipients. Agents for adjusting the pH value, buffers, agents for adjusting toxicity, and the like may also be included. In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

The vaccine of the present invention is surprisingly effective at relatively low doses. In particular embodiments, the single dose is from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU). Administration of low doses of this live bacterial vaccine minimizes the risk of excretion and thus of transmission to third parties.

In this context, the term "about" or "approximately" means within a factor of 3, alternatively within a factor of 2, including within a factor of 1.5 of a given value or range.

In particular embodiments, the attenuated strain of Salmonella is for use in individualized cancer immunotherapy comprising the step of measuring the expression of at least one tumor antigen and/or at least one tumor stroma antigen and/or the pre-immune response against at least one tumor antigen and/or at least one tumor stroma antigen of a patient, for example by companion diagnostics targeting the patient's specific tumor and/or stromal antigen pattern.

SHORT DESCRIPTION OF FIGURES

FIG. 1: Overview over Drug Product manufacture
FIG. 2: Flow chart of Drug Product manufacture
FIG. 3: Expression plasmid synthesis
FIG. 4: VXM04 Clones Growth Kinetics—$OD_{600}$
FIG. 5: VXM04 Clones Growth Kinetics—CFU/ml
FIG. 6: VXM04 Clones Growth Kinetics—pH in Culture Medium
FIG. 7: VXM08 Clones Growth Kinetics—$OD_{600}$
FIG. 8: VXM08 Clones Growth Kinetics—CFU/ml
FIG. 9: VXM08 Clones Growth Kinetics—pH in Culture Medium
FIG. 10: VXM01 Clones Growth Kinetics—$OD_{600}$
FIG. 11: VXM01 Clones Growth Kinetics—CFU/ml
FIG. 12: VXM01 Clones Growth Kinetics—pH in Culture Medium

EXAMPLES

Example 1: Synthesis of Antigen I Antigen Fragment Encoding cDNA

Synthesis of the cDNA inserts was performed by double strand in vitro gene synthesis. cDNAs encoding five different tumor antigens and one tumor stroma antigen were synthesized. The synthesized cDNAs are listed in Table 4.

TABLE 4

Synthesized antigen cDNAs

| cDNA | cDNA length | Antigen type | cDNA SEQ ID |
|---|---|---|---|
| Human wild type VEGFR-2 | 4071 bp | Full length wild type tumor stroma antigen | SEQ ID NO 9 |
| Human wild type MSLN | 1893 bp | Full length wild type tumor antigen | SEQ ID NO 11 |
| Human wild type CEA | 2109 bp | Full length wild type tumor antigen | SEQ ID NO 12 |
| Wild type human CMV pp65 | 1683 bp | Full length wild type tumor antigen | SEQ ID NO 13 |
| K436N mutated human CMV pp65 | 1683 bp | Full length mutated tumor antigen | SEQ ID NO 14 |
| Truncated K436N mutated human CMV pp65 | 1608 bp | Truncated mutated tumor antigen | SEQ ID NO 15 |

The sequences of the cDNAs to be synthesized were subdivided into individual oligonucleotides of 40-50 bases. The designed oligonucleotides overlap and correspond to both DNA strands. These oligonucleotides were prepared by chemical synthesis. The in vitro synthesized forward and reverse oligonucleotides were combined in Eppendorf tubes and 5'-phosphorylated by incubation with T4 polynucleotide kinase and ATP. The phosphorylated forward and reverse oligonucleotides were denatured at 95° C. Complementary oligonucleotides were annealed by progressive cooling (1°/min) of the mixture. After the annealing process the aligned oligonucleotides were ligated using thermostable Taq DNA ligase. The denaturing and annealing process was repeated several times in a thermocycler to resolve mismatched base pairs and achieve complete matching of the complementary strands over the full length of the fragments. To increase the yield of the ligated fragments, PCR was performed after completion of the ligation step using primers annealing at outward positions of the fragments. The PCR amplification products were isolated by preparative agarose gel electrophoresis.

Example 2: Cloning of Antigen cDNA into Expression Plasmid

The cDNAs synthesized in Example 1 were cloned into the plasmid pVAX10 via NheI/XhoI.

The thus generated recombinant plasmids were transformed into E. coli, isolated and sequenced. The complete sequences of the synthesized plasmids were determined and aligned to the corresponding reference sequences. The results of the sequence verification are summarized in Table 5.

TABLE 5

Sequence verification of recombinant plasmids

| cDNA | Identified mutations vs. reference sequence |
| --- | --- |
| Human wild type VEGFR-2 | none |
| Human wild type MSLN | 1 silent mutation |
| Human wild type CEA | none |
| Wild type human CMV pp65 | none |
| K436N mutated human CMV pp65 | none |
| Truncated K436N mutated human CMV pp65 | none |

One mismatch mutation was detected in the open reading frame for hMSLN at plasmid position 1392 (adenine instead of guanine) corresponding to position 657 in the cDNA. This mute mutation (wobble position) does not result in an altered consensus amino acid for MSLN. The mutated sequence was therefore accepted for transformation of *S. typhi* Ty21a and generation of the batch production clones. For all other plasmids the cloned sequences displayed 100% sequence identity to the reference sequences.

Example 3: Transformation of *S. typhi* Ty21a with Antigen Encoding Plasmids

*Salmonella typhi* Ty21a was transformed with the five recombinant plasmids obtained in Example 2. For that purpose, single *S. typhi* Ty21a colonies were picked from agar plates and grown in 100 mL TSB culture medium overnight at 37° C. The cultures were then formulated with 15% sterile glycerol, aliquoted (1 ml), labelled, frozen, and stored at −75° C.±5° C. as Master Cell Bank, pending use. Two of the isolates prepared, designated VAX.Ty21-1 and VAX.Ty21-2, were selected for further use.

The bacterial strain identity of the prepared isolates was verified by growing the isolates on bromothymol blue galactose agar and/or on Kligler iron agar. The characteristics of the obtained cell colonies used as Master Cell Bank is described in Table 6.

TABLE 6

Characterization Testing of the *Salmonella* Typhi Ty 21a Isolates for Use as Master Cell Bank

| Test Parameter | Test Method | Result VAX.Ty21-1 | VAX.Ty21-2 |
| --- | --- | --- | --- |
| Identity | BTB-Gal Agar | Conforms, green to yellowish colonies without discoloration of the medium | Conforms, green to yellowish colonies without discoloration of the medium |
| | Kligler Iron Agar | Conforms, yellow coloration of the medium, only little gas formation | Conforms, yellow coloration of the medium, only little gas formation |
| Content | CFU determination | $7.6 \times 10^8$ CFU/mL | $7.0 \times 10^8$ CFU/mL |

The isolate VAX.Ty21-1 was used as recipient strain for transformation with the recombinant plasmids generated in Example 2. The frozen glycerol stock of isolate VAX.Ty21-1 was streaked on LB agar plates (ACF soy peptone). One single colony was picked and cultivated in 3 ml of LB-medium (ACF soy peptone) overnight at 37° C. This culture was used to inoculate 2×300 ml LB-medium which was further incubated at 37° C. until the OD600 reached 0.5. In order to obtain competent cells for electroporation the culture was harvested by centrifugation at 4° C. The pellet was resuspended in 500 ml of ice cold $H_2O$ and centrifuged again. After two further washes in ice cold water/10% glycerol the pellet was resuspended in 2 ml of 10% glycerol (animal free), aliquoted (50 μl) and frozen on dry ice.

For transformation one aliquot of competent cells per recombinant plasmid was thawed and electroporated with 3-5 μl of recombinant plasmid DNA each. Following a brief incubation period in 1 ml of LB (ACF) medium at 37° C., the cell suspensions were streaked on LB (ACF) agar plates containing kanamycin (25 and 50 μg/ml). The plates were incubated at 37° C. overnight.

Three single colonies per transformation reaction were then selected and used to inoculate 3 ml of LB medium (ACF soy peptone) containing kanamycin (50 μg/ml). Cultures were incubated at 37° C. overnight. Plasmid DNA was isolated and plasmid identity was confirmed by restriction analysis.

The selected clones were expanded in LB medium containing 50 μg/ml kanamycin. Cultures were mixed with 10% (v/v) glycerol, aliquoted (1 ml) and stored frozen at −70° C. The plasmids of the recombinant Ty21a clones were isolated and complete sequencing was performed. 100% sequence identity of the plasmids of each of the selected clones with the reference sequence was confirmed except for the hMSLN clone were one silent point mutation was identified (see Tab. 5).

The generated transformed clones are listed in Table 7.

TABLE 7

Transformed Clones

| cDNA | Batch Production Clones |
| --- | --- |
| Human wild type VEGFR-2 | VXM01: VAX.11-01, VAX.11-02, VAX.21-01, VAX.21-02, VAX.21-03 |
| Human wild type MSLN | VXM04: VXM04_K06424, VXM04_K06425, VXM04_K06426 |
| Human wild type CEA | VXM08: VXM08h_K08.1.1, VXM08h_K08.2.2, VXM08h_K08.4.4 |
| Wild type human CMV pp65 | VXM65_1: h_VXM65_K_K65.3.3 |
| K436N mutated human CMV pp65 | VXM65_2: h_VXM65_N_K65.4.12 |
| Truncated K436N mutated human CMV pp65 | VXM65_3: h_VXM65_Nshort_K65.1.1 |

Example 4: Characterization of Transformed Cell Clones and Batch Production Clone Selection The following analytical parameters were evaluated for selection of the VXM01, VXM04 and VXM08 Batch Production Clones to be used for the establishment of the respective Drug Substances.

Growth kinetics over time upon culturing in selective medium determined by OD600, pH and CFU
Plasmid stability after cryo-conservation (% PS)
Plasmid DNA extraction and confirmation of identity by plasmid restriction analysis
Determination of antigen expression efficacy after transient transfection of plasmid DNA into a eukaryotic cell line The growth characteristics of the VXM01, VXM04 and VXM08 transformed clones listed in Table 7 were determined. All six VXM01 clones tested for growth expansion (VAX.11-01, VAX.11-02, VAX.21-01, VAX.21-02, VAX.21-03) grew well, but only clone VAX.11-02 grew to the same level as the Ty21a isolate from which it was derived. The growth characteristics of VXM04 clones VXM04_K06424, VXM04_K06425 and VXM04_K06426 are presented in FIG. 4, FIG. 5 and FIG. 6. All three clones displayed comparable growth rates in the culture medium with a slight growth advantage for clone VXM04_K06426. Regarding the VXM08 candidates (VXM08h_K08.1.1, VXM08h_K08.2.2 and VXM08h_K08.4.4), all clones displayed comparable growth characteristics, however, clone VXM08h_K08.1.1 was superior to the other two clones.

Testing of the six VXM01 clones revealed that plasmid stability of VAX.11-02 was highest followed by VAX.11-03 and VAX.21-02. No significant difference was apparent between the three VXM04 clones with respect to plasmid stability before and after freezing. Testing of the three VXM08 clones revealed that plasmid stability of VXM08h_K08.4.4 was highest followed by VXM08h_K08.1.1 and VXM08h_K08.2.2.

Restriction analysis of plasmid DNA isolated from each of the six VXM01 clones revealed the expected pattern of restriction fragments. Comparable amounts of plasmid DNA could be isolated from the three clones.

Restriction analysis of plasmid DNA isolated from each of the three VXM04 clones revealed the expected pattern of restriction fragments. Comparable amounts of plasmid DNA could be isolated from the three clones.

Restriction analysis of plasmid DNA isolated from each of the three VXM08 clones revealed the expected pattern of restriction fragments. Comparable amounts of plasmid DNA could be isolated from the three clones.

After transfection of HEK293T cells with plasmid DNA isolated from the six VXM01 clones and Western blot analysis of cell extracts all six clones expressed the VEGFR-2 protein, with VAX.11-02, VAX.11-03 and VAX.21-02 showing the highest level, and with VAX.11-02 exhibiting a trend towards higher expression level according to visual inspection of the bands in the Western Blot gel.

After transfection of HEK293T cells with plasmid DNA isolated from the three VXM04 clones and Western blot analysis of cell extracts three bands with apparent molecular weights of approximately 65 kDa, 40 kDa and 28 kDa were identified in each of the extracts. Based on staining intensity expression was highest when plasmid DNA isolated from clone 6316 was transfected.

After transfection of HEK293T cells with plasmid DNA isolated from the three VXM08 clones and Western blot analysis of cell extracts all 3 clones expressed the glycosylated human CEACAM5 protein, with clone VXM08h_K08.1.2 showing the highest level, according to visual inspection of the bands in the Western Blot gel.

Based on the data obtained from growth characteristics, plasmid stability, and protein expression studies, VAX.11-02 was selected as VXM01 Batch Production Clone for the preparation of the Drug Substance.

After consideration of the data obtained from growth characteristics, plasmid stability, and protein expression studies, clone VXM04_K06426 was selected as VXM04 Batch Production Clone for the preparation of the Drug Substance.

Based on the data obtained from growth characteristics, plasmid stability studies, clone VXM08h_K08.4.4 was selected as VXM08 Batch Production Clone for the preparation of the Drug Substance.

Example 5: Preparation and Release Testing of Drug Substances

The VXM01, VXM04 and VXM08 Drug Substances were manufactured in compliance with GMP requirements starting with a single colony of the selected Batch Production Clone each. Several cell suspension dilutions per Batch Production Clone were plated on TSB agar plates containing 25 µg/ml kanamycin (Preculture 1). The plates were incubated at 37° C. for 20-30 h. Upon completion of the incubation time, three single colonies each were selected and transferred to three 50 ml flasks containing TSB medium plus 25 µg/ml kanamycin (Preculture 2). Colonies were grown to a maximum OD600 of <1.0 for 9 h t 1 h at 30° C. Agitation of each flask was set at 120 rpm. The flask with the highest OD value was selected for further cultivation. A volume of 50 ml of the Preculture 2 was transferred to a flask containing 1000 mL TSB medium plus 25 µg/mL kanamycin (main culture). After incubation at 30° C. for 9 h t 1 h, with agitation set at 180 rpm, the bacteria were grown to a target OD600 between 0.9 and 1.5. Once the fermentation was completed, glycerol was added to the culture to a final concentration of 15% (w/w). The suspension was mixed and then aliquoted (1 ml) into 2 ml cryovials. The vials were labelled and frozen immediately at $-75°$ C.$\pm 5°$ C. for storage.

The thus prepared Drug Substances VXM01, VXM04 and VXM08 were then further tested to establish the respective final Drug Products (release specification). The release characterization of the Drug Substances was based on the acceptance criteria listed in Table 3.

5.1 Biochemical Profile

For direct plating of Ty21a and Drug Substances VXM01, VXM04 and VXM08 a loop of the completely thawed suspension was transferred to BTB-Gal-agar plates applying an appropriate streaking method to obtain single colonies. The inoculation of the control organism *P. aeruginosa* (ATCC 9027) and *S. typhimurium* (Moskau) was performed by transferring a bead of a Microbank® (storage system for microbial cultures) and subsequent streaking on the agar plate. For inoculation of KIA a loop (bead) of the same vial was first streaked onto the surface of the slant and then infeeded into the butt. The media were incubated for 48 h at 37° C.

The resulting colonies showed the expected colony morphology. All three drug substances VXM01, VXM04 and VXM08 showed colony growth in the presence of 1.25% galactose on bromothymol blue galactose agar. The colonies were light-blue transparent and/or green to yellowish and did not result in colour change of the medium.

5.2 Serotyping

A drop of antiserum (05 or 09) was transferred to a chamber slide. A loop of cell material of each Drug Substance to be tested was taken from the lower (wet) side of the KIA and placed next to the antiserum. The solutions were mixed with the loop. The resulting suspension was slightly turbid. The suspension was distributed by wiping of the chamber slides several times. The reactions were evaluated after 2 min against a black background.

All three drug substances VXM01, VXM04 and VXM08 complied with the expected 09-positive and 05-negative serotype.

5.3 Restriction Analysis

The recombinant plasmids were isolated from the Drug Substances VXM01, VXM04 and VXM08 and digested with two different digestion enzymes/combinations in separate reactions for an appropriate time. The reactions were stopped and analyzed on an agarose gel. The Endonucleases used for the restriction analysis are presented in Table 8.

TABLE 8

Set-Up for Restriction Analysis

| Drug Substance | Restriction Endonuclease | Expected Size of Fragments (base pairs) |
|---|---|---|
| VXM01 | StyI | 2209, 1453, 1196, 1094, 846, 623 and 159 |
| VXM01 | BamHI | 7580bp |
| VXM01 | BgtI | 2555, 2209, 1498 and 1318 |
| VXM04 | NheI/XhoI | 1899 and 3494 |
| VXM04 | NdeI | 1160 and 4233 |
| VXM08 | SacI | 4142, 933 and 534 |
| VXM08 | BamHI | 5609 |
| VXM08 | NheI/XhoI | 3494 and 2115 |

All three recombinant plasmids isolated from Drug Substances VXM01, VXM04 and WM08 showed the expected restriction pattern.

5.4 Sequence Analysis of the Plasmid

The recombinant plasmids isolated from Drug Substances VXM01, VXM04 and VXM08 were quantified. After retransformation in *E. coli*, the recombinant plasmids were again isolated, quantified and sequenced.

100% sequence identity of the three recombinant plasmids with their respective reference sequence was confirmed.

5.5 Expression Analysis

The recombinant plasmids were isolated from Drug Substances VXM01, VXM04 and VXM08 using a commercial DNA extraction and purification kit and the DNA content was determined. One day before transfection $7.5 \times 10^5$ 293 T cells were plated per well in 6-well plates to give a 90-95% confluence at the time of the assay. For transfection, the transfection complex consisting of the isolated plasmid DNA and Lipofectamine 2000™ was added to the cells and incubated for approximately 24 hours. After the incubation the cells were resuspended, washed once with PBS and lysed. Cell debris was pelleted by centrifugation. The supernatant was collected and protein content was determined. The samples were stored at −70° C. until Western Blot analysis was, performed. The presence of the recombinant proteins was demonstrated and compared on a semi-quantitative basis with appropriate reference material.

The expression levels of antigens VEGFR-2, MSLN and CEA were comparable to the chosen reference substance.

5.6 Viable Cell Number Determination

Serial dilutions of bacterial suspensions of Drug Substances VXM01, VXM04 and VXM08 down to a dilution factor of $10^{-8}$ were prepared and plated onto agar plates. After appropriate incubation colonies were counted. Counting was started, when colonies were clearly visible, but not too large.

The viable cell numbers determined are listed in Table 9.

TABLE 9

Viable cell numbers

| Drug Substance | Viable cell number |
|---|---|
| VXM01 | $3 \times 10^8$ CFU/ml |
| VXM04 | $5.5 \times 10^9$ CFU/ml |
| VXM08 | $2.5 \times 10^9$ CFU/ml |

5.7 Plasmid Stability

Serial dilutions of bacterial suspensions of Drug Substances VXM01, VXM04 and VXM08 (the same vials used for viable cell count testing) were prepared and plated onto TSB plates containing the antibiotic kanamycin. After appropriate incubation colonies were counted. Counting started, when colonies were clearly visible, but not too large. Plasmid stability was calculated by comparing colony forming units on TSB with and without kanamycin as follows:

$$PST=(CFU \text{ with kanamycin}/CFU \text{ without kanamycin}) \times 100$$

All three Drug Substances VXM01, VXM04 and VXM08 complied with the pre-set plasmid stability acceptance criterion as specified in Table 3. The determined plasmid stability of all three recombinant plasmids was at least 75%.

5.8 Microbial Impurities

To determine counts of total aerobic bacteria, molds and fungi and confirm the absence of the specific germs *Escherichia coli, Salmonella* sp., *Pseudomonas aeruginosa, Staphylococcus aureus*, and *Clostridium* sp. the Drug Substances VXM01, VXM04 and VXM08 were tested according to the European Pharmacopoeia Ph. Eur. monographs 2.6.12 and 2.16.13.

All three Drug Substances VXM01, VXM04 and VXM08 complied with the pre-set microbial impurity acceptance criterion as specified in Table 3. In all three Drug Substances VXM01, VXM04 and VXM08 the total aerobic microbial count (TAMC) was not more than $10^2$ CFU/ml, the total yeast and mold count (TYMC) was not more than 2 CFU/ml and *P. aeruginosa, S. aureus, E. coli, Clostridium* sp. and other *Salmonella* strains were not detectable in 1 ml cell suspension.

5.9 Bacteriophage Testing

The testing procedure for the detection of bacteriophages employed plating in soft-agar overlays containing an appropriate host and either the sample to be tested or a control suspension of phages. To improve the sensitivity of the assay a preceding enrichment step was included. In this step the samples were incubated for 4 h with appropriate host cells. Subsequently, one sample of each of these enrichment cultures was plated.

All three Drug Substances VXM01, VXM04 and VXM08 complied with the pre-set purity of phage acceptance criterion as specified in Table 3. No phages were detectable in 100 µl of cell suspension after the enrichment step.

SEQUENCE TABLE

SEQ ID NO 1: expression plasmid
SEQ ID NO 2: amino acid sequence VEGFR-2
SEQ ID NO 3: amino acid sequence WT1
SEQ ID NO 4: amino acid sequence MSLN
SEQ ID NO 5: amino acid sequence CEA
SEQ ID NO 6: amino acid sequence CMV pp65
SEQ ID NO 7: amino acid sequence CMV pp65
SEQ ID NO 8: amino acid sequence CMV pp65
SEQ ID NO 9: cDNA VEGFR-2
SEQ ID NO 10: cDNA WT1
SEQ ID NO 11: cDNA MSLN
SEQ ID NO 12: cDNA CEA
SEQ ID NO 13: cDNA CMVpp65
SEQ ID NO 14: cDNA CMVpp65
SEQ ID NO 15: cDNA CMVpp65

The invention claimed is:

1. Method for producing a DNA vaccine for cancer immunotherapy comprising at least the following steps:
- a) transforming an attenuated strain of *Salmonella* with at least one DNA molecule comprising at least one eukaryotic expression cassette encoding at least one antigen or at least one fragment thereof;
- b) characterizing at least one transformed cell clone obtained in step (a);
- c) selecting at least one of the transformed cell clone(s) characterized in step (b) and further characterizing said at least one selected transformed cell clone;

wherein step (b) comprises at least one of the following substeps:
- bi) assessing the cell growth of at least one transformed cell clone obtained in step (a) over time;
- bii) assessing the stability of the at least one DNA molecule comprising at least one expression cassette encoding at least one antigen or at least one fragment thereof in the at least one transformed cell clone obtained in step (a);
- biii) isolating the at least one DNA molecule comprising at least one expression cassette encoding at least one antigen or at least one fragment thereof from at least one transformed cell clone obtained in step (a) and characterizing the at least one isolated DNA molecule by restriction analysis and/or sequencing;
- biv) isolating the at least one DNA molecule comprising at least one expression cassette encoding at least one antigen or at least one fragment thereof from at least one transformed cell clone obtained in step (a), transfecting the at least one isolated DNA molecule into at least one eukaryotic cell and assessing the expression of the at least one antigen or the at least one fragment thereof in said at least one eukaryotic cell;

wherein step (c) comprises at least one of the following substeps:
- ci) assessing the number of viable cells per ml cell suspension of the at least one transformed cell clone selected in step (c);
- cii) assessing the stability of the at least one DNA molecule comprising at least one expression cassette encoding at least one antigen or at least one fragment thereof in the at least one transformed cell clone selected in step (c);

ciii) isolating the at least one DNA molecule comprising at least one expression cassette encoding at least one antigen or at least one fragment thereof from the at least one transformed cell clone selected in step (c) and characterizing the at least one isolated DNA molecule by restriction analysis and/or sequencing;

civ) isolating the at least one DNA molecule comprising at least one expression cassette encoding at least one antigen or at least one fragment thereof from the at least one transformed cell clone selected in step (c), transfecting the at least one isolated DNA molecule into at least one eukaryotic cell and assessing the expression of the at least one antigen or the at least one fragment thereof in said at least one eukaryotic cell;

cv) testing for the presence of bacterial, fungal and/or viral contaminants in at the least one transformed cell clone selected in step (c);

cvi) verifying the bacterial strain identity of the at least one transformed cell clone selected in step (c); and wherein the attenuated strain of *Salmonella* is *Salmonella typhi* Ty21a.

2. The method of claim 1, wherein said at least one antigen is selected from the group consisting of a tumor antigen and a tumor stroma antigen.

3. The method of claim 1, wherein said at least one DNA molecule comprises the kanamycin antibiotic resistance gene, the pMB1 ori, and a eukaryotic expression cassette encoding said antigen under the control of a CMV promoter, wherein said DNA molecule is a DNA plasmid.

4. The method of claim 1, wherein in step (a) said attenuated strain of *Salmonella* is transformed by electroporation with said at least one DNA molecule comprising at least one expression cassette encoding at least one antigen or at least one fragment thereof.

5. The method of claim 1, wherein step (b) comprises one, two, three, or all four of said substeps (bi), (bii), (biii) and (biv).

6. The method of claim 1, wherein step (c) comprises one, two, three, four, five, or all six of said substeps (ci), (cii), (ciii), (civ), (cv) and (cvi).

7. The method of claim 1, wherein in step (cv) the presence of bacterial and/or fungal contaminants is tested by growing the at least one transformed cell clone selected in step (c) in or on at least one suitable selective medium.

8. The method of claim 1, wherein in step (cvi) the bacterial strain identity is verified by growing the at least one transformed cell clone selected in step (c) on bromothymol blue galactose agar and/or on Kligler iron agar and/or by assessing the presence of *Salmonella* 05 and/or 09-surface antigen(s).

9. The method of claim 1, wherein the at least one antigen is a tumor antigen and wherein the tumor antigen is a neoantigen.

10. The method of claim 1, wherein the at least one antigen fragment comprises from 1 to 25 epitopes.

11. The method of claim 1, wherein the at least one tumor antigen and/or tumor stroma antigen is a patient specific tumor antigen and/or tumor stroma antigen.

12. The method of claim 11, wherein the at least one tumor antigen and/or stroma antigen was shown to be expressed by tumor cells or the tumor stroma cells of one specific patient.

13. The method of claim 12, wherein the at least one patient specific tumor antigen and/or tumor stroma antigen was identified by assessing the expression profile of a patient's tumor and/or tumor stroma either on mRNA or on protein level or by assessing pre-existing T cell immune responses to tumor antigens and/or stroma cells of a patient.

* * * * *

SEQUENCE LISTING

<160> NUMBER OF SEQ ID NOS: 15

<210> SEQ ID NO 1
<211> LENGTH: 3500
<212> TYPE: DNA
<213> ORGANISM: Artificial Sequence
<220> FEATURE:
<223> OTHER INFORMATION: expression plasmid

<400> SEQUENCE: 1

```
tgggcttttg ctggcctttt gctcacatgt tcttgactct tcgcgatgta cgggccagat      60
atacgcgttg acattgatta ttgactagtt attaatagta atcaattacg gggtcattag     120
ttcatagccc atatatggag ttccgcgtta cataacttac ggtaaatggc ccgcctggct     180
gaccgcccaa cgacccccgc ccattgacgt caataatgac gtatgttccc atagtaacgc     240
caatagggac tttccattga cgtcaatggg tggactattt acggtaaact gcccacttgg     300
cagtacatca agtgtatcat atgccaagta cgccccctat tgacgtcaat gacggtaaat     360
ggcccgcctg gcattatgcc cagtacatga ccttatggga ctttcctact tggcagtaca     420
tctacgtatt agtcatcgct attaccatgg tgatgcggtt ttggcagtac atcaatgggc     480
gtggatagcg gtttgactca cggggatttc caagtctcca ccccattgac gtcaatggga     540
gtttgttttg gcaccaaaat caacgggact ttccaaaatg tcgtaacaac tccgccccat     600
tgacgcaaat gggcggtagg cgtgtacggt gggaggtcta taagcagag ctctctggc      660
taactagaga acccactgct tactggctta tcgaaattaa tacgactcac tatagggaga     720
cccaagctgg ctagcctcga gtctagaggg cccgtttaaa cccgctgatc agcctcgact     780
gtgccttcta gttgccagcc atctgttgtt tgccctcccc cgtgccttc cttgaccctg     840
gaaggtgcca ctcccactgt cctttcctaa taaaatgagg aaattgcatc gcattgtctg     900
agtaggtgtc attctattct ggggggtggg gtggggcagg acagcaaggg ggaggattgg     960
gaagacaata gcaggcatgc tggggatgcg gtgggctcta tggcttctac tgggcggttt    1020
tatgacagc aagcgaaccg gaattgccag ctggggcgcc ctctggtaag gttgggaagc     1080
cctgcaaagt aaactggatg gctttctcgc cgccaaggat ctgatggcgc aggggatcaa    1140
gctctgatca agagacagga tgaggatcgt ttcgcatgat tgaacaagat ggattgcacg    1200
caggttctcc ggccgcttgg gtggagaggc tattcggcta tgactgggca acagacaa     1260
tcggctgctc tgatgccgcc gtgttccggc tgtcagcgca ggggcgcccg gttcttttg     1320
tcaagaccga cctgtccggt gccctgaatg aactgcaaga cgaggcagcg cggctatcgt    1380
ggctggccac gacgggcgtt ccttgcgcag ctgtgctcga cgttgtcact gaagcgggaa    1440
gggactggct gctattgggc gaagtgccgg ggcaggatct cctgtcatct caccttgctc    1500
ctgccgagaa agtatccatc atggctgatg caatgcggcg gctgcatacg cttgatccgg    1560
ctacctgccc attcgaccac caagcgaaac atcgcatcga gcgagcacgt actcggatgg    1620
aagccggtct tgtcgatcag gatgatctgg acgaagagca tcaggggctc gcgccagccg    1680
aactgttcgc caggctcaag gcgagcatgc ccgacggcga gatctcgtc gtgacccatg    1740
gcgatgcctg cttgccgaat atcatggtgg aaaatggccg cttttctgga ttcatcgact    1800
gtggccggct gggtgtggcg gaccgctatc aggacatagc gttggctacc cgtgatattg    1860
ctgaagagct tggcggcgaa tgggctgacc gcttcctcgt gctttacggt atcgccgctc    1920
ccgattcgca gcgcatcgcc ttctatcgcc ttcttgacga gttcttctga attattaacg    1980
cttacaattt cctgatgcgg tattttctcc ttacgcatct gtgcggtatt tcacaccgca    2040
```

```
tacaggtggc acttttcggg gaaatgtgcg cggaaccccct atttgtttat ttttctaaat    2100
acattcaaat atgtatccgc tcatgagaca ataaccctga taaatgcttc aataatagca    2160
cgtgctaaaa cttcattttt aatttaaaag gatctaggtg aagatccttt ttgataatct    2220
catgaccaaa atcccttaac gtgagttttc gttccactga gcgtcagacc cccatcagtg    2280
accaaacagg aaaaaaccgc ccttaacatg gcccgcttta tcagaagcca gacattaacg    2340
cttctggaga aactcaacga gctggacgcg gatgaacagg cagacatctg tgaatcgctt    2400
cacgaccacg ctgatgagct ttaccgcagc tgcctcgcgc gtttcggtga tgacggtgaa    2460
aacctctgac acatgcagct cccggagacg gtcacagctt gtctgtaagc ggatgccggg    2520
agcagacaag cccgtcaggg cgcgtcagcg ggtgttggcg ggtgtcgggg cgcagccatg    2580
acccagtcac gtagcgatag cggagtgtat actggcttaa ctatgcggca tcagagcaga    2640
ttgtactgag agtgcaccat atgcggtgtg aaataccgca cagatgcgta aggagaaaat    2700
accgcatcag gcgctcttcc gcttcctcgc tcactgactc gctgcgctcg gtcgttcggc    2760
tgcggcgagc ggtatcagct cactcaaagg cggtaatacg gttatccaca gaatcagggg    2820
ataacgcagg aaagaacatg tgagcaaaag gccagcaaaa ggccaggaac cgtaaaaagg    2880
ccgcgttgct ggcgtttttc cataggctcc gcccccctga cgagcatcac aaaaatcgac    2940
gctcaagtca gaggtggcga aacccgacag gactataaag ataccaggcg tttccccctg    3000
gaagctccct cgtgcgctct cctgttccga ccctgccgct taccggatac ctgtccgcct    3060
ttctcccttc gggaagcgtg gcgctttctc atagctcacg ctgtaggtat ctcagttcgg    3120
tgtaggtcgt tcgctccaag ctgggctgtg tgcacgaacc ccccgttcag cccgaccgct    3180
gcgccttatc cggtaactat cgtcttgagt ccaacccggt aagacacgac ttatcgccac    3240
tggcagcagc cactggtaac aggattagca gagcgaggta tgtaggcggt gctacagagt    3300
tcttgaagtg gtggcctaac tacggctaca ctagaaggac agtatttggt atctgcgctc    3360
tgctgaagcc agttaccttc ggaaaaagag ttggtagctc ttgatccggc aaacaaacca    3420
ccgctggtag cggtggtttt tttgtttgca agcagcagat tacgcgcaga aaaaaaggat    3480
ctcaagaaga tcctttgatc                                              3500
```

<210> SEQ ID NO 2
<211> LENGTH: 1356
<212> TYPE: PRT
<213> ORGANISM: Homo sapiens

<400> SEQUENCE: 2

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110
```

```
Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
        180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
        260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
        340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
        500                 505                 510

Thr Val Ser Thr Leu Val Ile Gln Ala Ala Asn Val Ser Ala Leu Tyr
        515                 520                 525
```

```
            Lys Cys Glu Ala Val Asn Lys Val Gly Arg Gly Glu Arg Val Ile Ser
                530                 535                 540

Phe His Val Thr Arg Gly Pro Glu Ile Thr Leu Gln Pro Asp Met Gln
            545                 550                 555                 560

Pro Thr Glu Gln Glu Ser Val Ser Leu Trp Cys Thr Ala Asp Arg Ser
                                565                 570                 575

Thr Phe Glu Asn Leu Thr Trp Tyr Lys Leu Gly Pro Gln Pro Leu Pro
                            580                 585                 590

Ile His Val Gly Glu Leu Pro Thr Pro Val Cys Lys Asn Leu Asp Thr
                        595                 600                 605

Leu Trp Lys Leu Asn Ala Thr Met Phe Ser Asn Ser Thr Asn Asp Ile
                    610                 615                 620

Leu Ile Met Glu Leu Lys Asn Ala Ser Leu Gln Asp Gln Gly Asp Tyr
            625                 630                 635                 640

Val Cys Leu Ala Gln Asp Arg Lys Thr Lys Lys Arg His Cys Val Val
                                645                 650                 655

Arg Gln Leu Thr Val Leu Glu Arg Val Ala Pro Thr Ile Thr Gly Asn
                            660                 665                 670

Leu Glu Asn Gln Thr Thr Ser Ile Gly Glu Ser Ile Glu Val Ser Cys
                        675                 680                 685

Thr Ala Ser Gly Asn Pro Pro Pro Gln Ile Met Trp Phe Lys Asp Asn
                    690                 695                 700

Glu Thr Leu Val Glu Asp Ser Gly Ile Val Leu Lys Asp Gly Asn Arg
            705                 710                 715                 720

Asn Leu Thr Ile Arg Arg Val Arg Lys Glu Asp Glu Gly Leu Tyr Thr
                                725                 730                 735

Cys Gln Ala Cys Ser Val Leu Gly Cys Ala Lys Val Glu Ala Phe Phe
                            740                 745                 750

Ile Ile Glu Gly Ala Gln Glu Lys Thr Asn Leu Glu Ile Ile Ile Leu
                        755                 760                 765

Val Gly Thr Ala Val Ile Ala Met Phe Phe Trp Leu Leu Leu Val Ile
                    770                 775                 780

Ile Leu Arg Thr Val Lys Arg Ala Asn Gly Gly Glu Leu Lys Thr Gly
            785                 790                 795                 800

Tyr Leu Ser Ile Val Met Asp Pro Asp Glu Leu Pro Leu Asp Glu His
                                805                 810                 815

Cys Glu Arg Leu Pro Tyr Asp Ala Ser Lys Trp Glu Phe Pro Arg Asp
                            820                 825                 830

Arg Leu Lys Leu Gly Lys Pro Leu Gly Arg Gly Ala Phe Gly Gln Val
                        835                 840                 845

Ile Glu Ala Asp Ala Phe Gly Ile Asp Lys Thr Ala Thr Cys Arg Thr
                    850                 855                 860

Val Ala Val Lys Met Leu Lys Glu Gly Ala Thr His Ser Glu His Arg
            865                 870                 875                 880

Ala Leu Met Ser Glu Leu Lys Ile Leu Ile His Ile Gly His His Leu
                                885                 890                 895

Asn Val Val Asn Leu Leu Gly Ala Cys Thr Lys Pro Gly Gly Pro Leu
                            900                 905                 910

Met Val Ile Val Glu Phe Cys Lys Phe Gly Asn Leu Ser Thr Tyr Leu
                        915                 920                 925

Arg Ser Lys Arg Asn Glu Phe Val Pro Tyr Lys Thr Lys Gly Ala Arg
                    930                 935                 940

Phe Arg Gln Gly Lys Asp Tyr Val Gly Ala Ile Pro Val Asp Leu Lys
```

```
            945                 950                 955                 960
Arg Arg Leu Asp Ser Ile Thr Ser Ser Gln Ser Ser Ala Ser Ser Gly
                    965                 970                 975
Phe Val Glu Glu Lys Ser Leu Ser Asp Val Glu Glu Glu Glu Ala Pro
                    980                 985                 990
Glu Asp Leu Tyr Lys Asp Phe Leu Thr Leu Glu His Leu Ile Cys Tyr
                    995                 1000                1005
Ser Phe Gln Val Ala Lys Gly Met Glu Phe Leu Ala Ser Arg Lys Cys
            1010                1015                1020
Ile His Arg Asp Leu Ala Ala Arg Asn Ile Leu Leu Ser Glu Lys Asn
1025                1030                1035                1040
Val Val Lys Ile Cys Asp Phe Gly Leu Ala Arg Asp Ile Tyr Lys Asp
                    1045                1050                1055
Pro Asp Tyr Val Arg Lys Gly Asp Ala Arg Leu Pro Leu Lys Trp Met
                    1060                1065                1070
Ala Pro Glu Thr Ile Phe Asp Arg Val Tyr Thr Ile Gln Ser Asp Val
                    1075                1080                1085
Trp Ser Phe Gly Val Leu Leu Trp Glu Ile Phe Ser Leu Gly Ala Ser
                    1090                1095                1100
Pro Tyr Pro Gly Val Lys Ile Asp Glu Glu Phe Cys Arg Arg Leu Lys
1105                1110                1115                1120
Glu Gly Thr Arg Met Arg Ala Pro Asp Tyr Thr Thr Pro Glu Met Tyr
                    1125                1130                1135
Gln Thr Met Leu Asp Cys Trp His Gly Glu Pro Ser Gln Arg Pro Thr
                    1140                1145                1150
Phe Ser Glu Leu Val Glu His Leu Gly Asn Leu Leu Gln Ala Asn Ala
                    1155                1160                1165
Gln Gln Asp Gly Lys Asp Tyr Ile Val Leu Pro Ile Ser Glu Thr Leu
            1170                1175                1180
Ser Met Glu Glu Asp Ser Gly Leu Ser Leu Pro Thr Ser Pro Val Ser
1185                1190                1195                1200
Cys Met Glu Glu Glu Glu Val Cys Asp Pro Lys Phe His Tyr Asp Asn
                    1205                1210                1215
Thr Ala Gly Ile Ser Gln Tyr Leu Gln Asn Ser Lys Arg Lys Ser Arg
                    1220                1225                1230
Pro Val Ser Val Lys Thr Phe Glu Asp Ile Pro Leu Glu Glu Pro Glu
                    1235                1240                1245
Val Lys Val Ile Pro Asp Asp Asn Gln Thr Asp Ser Gly Met Val Leu
            1250                1255                1260
Ala Ser Glu Glu Leu Lys Thr Leu Glu Asp Arg Thr Lys Leu Ser Pro
1265                1270                1275                1280
Ser Phe Gly Gly Met Val Pro Ser Lys Ser Arg Glu Ser Val Ala Ser
                    1285                1290                1295
Glu Gly Ser Asn Gln Thr Ser Gly Tyr Gln Ser Gly Tyr His Ser Asp
                    1300                1305                1310
Asp Thr Asp Thr Thr Val Tyr Ser Ser Glu Glu Ala Glu Leu Leu Lys
            1315                1320                1325
Leu Ile Glu Ile Gly Val Gln Thr Gly Ser Thr Ala Gln Ile Leu Gln
            1330                1335                1340
Pro Asp Ser Gly Thr Thr Leu Ser Ser Pro Pro Val
1345                1350                1355

<210> SEQ ID NO 3
```

```
<211> LENGTH: 371
<212> TYPE: PRT
<213> ORGANISM: Homo sapiens

<400> SEQUENCE: 3

Met Gly Ser Asp Val Arg Asp Leu Asn Ala Leu Leu Pro Ala Val
1               5                   10                  15

Ser Leu Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
            130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys
    370
```

<210> SEQ ID NO 4
<211> LENGTH: 630
<212> TYPE: PRT
<213> ORGANISM: Homo sapiens

<400> SEQUENCE: 4

```
Met Ala Leu Pro Thr Ala Arg Pro Leu Gly Ser Cys Gly Thr Pro
1               5                   10                  15

Ala Leu Gly Ser Leu Leu Phe Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380
```

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
            405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
610                 615                 620

Leu Ala Ser Thr Leu Ala
625                 630

<210> SEQ ID NO 5
<211> LENGTH: 702
<212> TYPE: PRT
<213> ORGANISM: Homo sapiens

<400> SEQUENCE: 5

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
65              70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

```
Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
            195                 200                 205

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
            275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
            355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
            450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
530                 535                 540
```

```
Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
690                 695                 700

<210> SEQ ID NO 6
<211> LENGTH: 561
<212> TYPE: PRT
<213> ORGANISM: Cytomegalovirus

<400> SEQUENCE: 6

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220
```

-continued

```
Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
            245                 250                 255

Thr Arg Asn Pro Gln Pro Phe Met Arg Pro His Glu Arg Asn Gly Phe
        260                 265                 270

Thr Val Leu Cys Pro Lys Asn Met Ile Ile Lys Pro Gly Lys Ile Ser
    275                 280                 285

His Ile Met Leu Asp Val Ala Phe Thr Ser His Glu His Phe Gly Leu
290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
            325                 330                 335

Val Glu Leu Arg Gln Tyr Asp Pro Val Ala Ala Leu Phe Phe Phe Asp
        340                 345                 350

Ile Asp Leu Leu Leu Gln Arg Gly Pro Gln Tyr Ser Glu His Pro Thr
    355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
            405                 410                 415

Thr Pro Arg Val Thr Gly Gly Gly Ala Met Ala Gly Ala Ser Thr Ser
        420                 425                 430

Ala Gly Arg Lys Arg Lys Ser Ala Ser Ser Ala Thr Ala Cys Thr Ala
    435                 440                 445

Gly Val Met Thr Arg Gly Arg Leu Lys Ala Glu Ser Thr Val Ala Pro
450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
            485                 490                 495

Val Pro Met Val Ala Thr Val Gln Gly Gln Asn Leu Lys Tyr Gln Glu
        500                 505                 510

Phe Phe Trp Asp Ala Asn Asp Ile Tyr Arg Ile Phe Ala Glu Leu Glu
    515                 520                 525

Gly Val Trp Gln Pro Ala Ala Gln Pro Lys Arg Arg Arg His Arg Gln
530                 535                 540

Asp Ala Leu Pro Gly Pro Cys Ile Ala Ser Thr Pro Lys Lys His Arg
545                 550                 555                 560

Gly

<210> SEQ ID NO 7
<211> LENGTH: 561
<212> TYPE: PRT
<213> ORGANISM: Cytomegalovirus

<400> SEQUENCE: 7

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30
```

```
Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
            115                 120                 125

His His Tyr Pro Ser Ala Ala Glu Arg Lys His Arg His Leu Pro Val
        130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
        210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
        290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
            355                 360                 365

Phe Thr Ser Gln Tyr Arg Ile Gln Gly Lys Leu Glu Tyr Arg His Thr
        370                 375                 380

Trp Asp Arg His Asp Glu Gly Ala Ala Gln Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
            420                 425                 430

Ala Gly Arg Asn Arg Lys Ser Ala Ser Ser Ala Thr Ala Cys Thr Ala
            435                 440                 445
```

```
Gly Val Met Thr Arg Gly Arg Leu Lys Ala Glu Ser Thr Val Ala Pro
            450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
            530                 535                 540

Asp Ala Leu Pro Gly Pro Cys Ile Ala Ser Thr Pro Lys Lys His Arg
545                 550                 555                 560

Gly

<210> SEQ ID NO 8
<211> LENGTH: 536
<212> TYPE: PRT
<213> ORGANISM: Cytomegalovirus

<400> SEQUENCE: 8

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
            35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255
```

```
Thr Arg Asn Pro Gln Pro Phe Met Arg Pro His Glu Arg Asn Gly Phe
        260                 265                 270

Thr Val Leu Cys Pro Lys Asn Met Ile Ile Lys Pro Gly Lys Ile Ser
    275                 280                 285

His Ile Met Leu Asp Val Ala Phe Thr Ser His Glu His Phe Gly Leu
290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
        340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
        420                 425                 430

Ala Gly Arg Asn Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
        500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln
530                 535

<210> SEQ ID NO 9
<211> LENGTH: 4071
<212> TYPE: DNA
<213> ORGANISM: Artificial Sequence
<220> FEATURE:
<223> OTHER INFORMATION: cDNA human VEGFR-2

<400> SEQUENCE: 9
atgcagagca aggtgctgct ggccgtcgcc ctgtggctct gcgtggagac ccgggccgcc      60
tctgtgggtt tgcctagtgt ttctcttgat ctgcccaggc tcagcataca aaaagacata     120
cttacaatta aggctaatac aactcttcaa attacttgca ggggacagag ggacttggac     180 tggcttggc ccaataatca gagtggcagt gagcaagggg tggaggtgac tgagtgcagc     240
gatggcctct tctgtaagac actcacaatt ccaaaagtga tcggaaatga cactggagcc     300
tacaagtgct tctaccggga aactgacttg gcctcggtca tttatgtcta tgttcaagat     360
tacagatctc catttattgc ttctgttagt gaccaacatg gagtcgtgta cattactgag     420
aacaaaaaca aaactgtggt gattccatgt ctcgggtcca tttcaaatct caacgtgtca     480
```

```
ctttgtgcaa gatacccaga aaagagattt gttcctgatg gtaacagaat ttcctgggac   540
agcaagaagg gctttactat tcccagctac atgatcagct atgctggcat ggtcttctgt   600
gaagcaaaaa ttaatgatga aagttaccag tctattatgt acatagttgt cgttgtaggg   660
tataggattt atgatgtggt tctgagtccg tctcatggaa ttgaactatc tgttggagaa   720
aagcttgtct taaattgtac agcaagaact gaactaaatg tggggattga cttcaactgg   780
gaataccctt cttcgaagca tcagcataag aaacttgtaa accgagacct aaaacccag    840 tctgggagtg agatgaagaa attttttgagc accttaacta tagatggtgt aacccggagt   900
gaccaaggat tgtacacctg tgcagcatcc agtgggctga tgaccaagaa gaacagcaca   960
tttgtcaggg tccatgaaaa acctttttgtt gcttttggaa gtggcatgga atctctggtg  1020
gaagccacgt gggggagcg tgtcagaatc cctgcgaagt accttggtta cccacccca   1080 gaaataaaat ggtataaaaa tggaataccc cttgagtcca atcacacaat taaagcgggg  1140
catgtactga cgattatgga agtgagtgaa agagacacag gaaattacac tgtcatcctt  1200
accaatccca tttcaaagga gaagcagagc catgtggtct ctctggttgt gtatgtccca  1260
ccccagattg gtgagaaatc tctaatctct cctgtggatt cctaccagta cggcaccact  1320
caaacgctga catgtacggt ctatgccatt cctcccccgc atcacatcca ctggtattgg  1380
cagttggagg aagagtgcgc caacgagccc agccaagctg tctcagtgac aaacccatac  1440
ccttgtgaag aatggagaag tgtggaggac ttccagggag gaaataaaat tgaagttaat  1500
aaaaatcaat ttgctctaat tgaaggaaaa aacaaaactg taagtaccct tgttatccaa  1560
gcggcaaatg tgtcagcttt gtacaaatgt gaagcggtca acaaagtcgg agaggagag   1620 agggtgatct ccttccacgt gaccagggt cctgaaatta ctttgcaacc tgacatgcag   1680
cccactgagc aggagagcgt gtctttgtgg tgcactgcag acagatctac gtttgagaac  1740
ctcacatggt acaagcttgg cccacagcct ctgccaatcc atgtgggaga gttgcccaca  1800 cctgttttgca agaacttgga tactctttgg aaattgaatg ccaccatgtt ctctaatagc  1860
acaaatgaca ttttgatcat ggagcttaag aatgcatcct gcaggacca aggagactat  1920 gtctgccttg ctcaagacag gaagaccaag aaaagacatt gcgtggtcag gcagctcaca  1980
gtcctagagc gtgtggcacc cacgatcaca ggaaacctgg agaatcagac gacaagtatt  2040
ggggaaagca tcgaagtctc atgcacggca tctgggaatc cccctccaca gatcatgtgg  2100
tttaaagata tgagaccct tgtagaagac tcaggcattg tattgaagga tgggaaccgg  2160
aacctcacta tccgcagagt gaggaaggag gacgaaggcc tctacacctg ccaggcatgc  2220
agtgttcttg gctgtgcaaa agtggaggca ttttttcataa tagaaggtgc ccaggaaag   2280 acgaacttgg aaaatcattat tctagtaggc acggcggtga ttgccatgtt cttctggcta  2340
cttcttgtca tcatcctacg gaccgttaag cgggccaatg gagggaact gaagacaggc  2400 tacttgtcca tcgtcatgga tccagatgaa ctcccattgg atgaacattg tgaacgactg  2460
ccttatgatg ccagcaaatg ggaattcccc agagaccggc tgaagctagg taagcctctt  2520
ggccgtggtg cctttggcca agtgattgaa gcagatgcct ttggaattga caagacagca  2580
acttgcagga cagtagcagt caaaatgttg aaagaaggag caacacacag tgagcatcga  2640
gctctcatgt ctgaactcaa gatcctcatt catattggtc accatctcaa tgtggtcaac  2700
cttctaggtg cctgtaccaa gccaggaggg ccactcatgg tgattgtgga attctgcaaa  2760
tttggaaacc tgtccactta cctgaggagc aagagaaatg aatttgtccc ctacaagacc  2820
```

-continued

| | |
|---|---|
| aaagggcac gattccgtca agggaaagac tacgttggag caatccctgt ggatctgaaa | 2880 |
| cggcgcttgg acagcatcac cagtagccag agctcagcca gctctggatt tgtggaggag | 2940 |
| aagtccctca gtgatgtaga agaagaggaa gctcctgaag atctgtataa ggacttcctg | 3000 |
| accttggagc atctcatctg ttacagcttc caagtggcta agggcatgga gttcttggca | 3060 |
| tcgcgaaagt gtatccacag ggacctggcg gcacgaaata tcctcttatc ggagaagaac | 3120 |
| gtggttaaaa tctgtgactt tggcttggcc cgggatattt ataaagatcc agattatgtc | 3180 |
| agaaaaggag atgctcgcct ccctttgaaa tggatggccc cagaaacaat ttttgacaga | 3240 |
| gtgtacacaa tccagagtga cgtctggtct tttggtgttt tgctgtggga aatattttcc | 3300 |
| ttaggtgctt ctccatatcc tggggtaaag attgatgaag aattttgtag gcgattgaaa | 3360 |
| gaaggaacta gaatgagggc ccctgattat actacaccag aaatgtacca gaccatgctg | 3420 |
| gactgctggc acggggagcc cagtcagaga cccacgtttt cagagttggt ggaacatttg | 3480 |
| ggaaatctct gcaagctaa tgctcagcag gatggcaaag actacattgt tcttccgata | 3540 |
| tcagagactt tgagcatgga agaggattct ggactctctc tgcctacctc acctgtttcc | 3600 |
| tgtatggagg aggaggaagt atgtgacccc aaattccatt atgacaacac agcaggaatc | 3660 |
| agtcagtatc tgcagaacag taagcgaaag agccggcctg tgagtgtaaa aacatttgaa | 3720 |
| gatatcccgt tagaagaacc agaagtaaaa gtaatcccag atgacaacca gacggacagt | 3780 |
| ggtatggttc ttgcctcaga agagctgaaa actttggaag acagaaccaa attatctcca | 3840 |
| tcttttggtg gaatggtgcc cagcaaaagc agggagtctg tggcatctga aggctcaaac | 3900 |
| cagacaagcg gctaccagtc cggatatcac tccgatgaca cagacaccac cgtgtactcc | 3960 |
| agtgaggaag cagaactttt aaagctgata gagattggag tgcaaaccgg tagcacagcc | 4020 |
| cagattctcc agcctgactc ggggaccaca ctgagctctc tcctgtttta a | 4071 |

<210> SEQ ID NO 10
<211> LENGTH: 1116
<212> TYPE: DNA
<213> ORGANISM: Artificial Sequence
<220> FEATURE:
<223> OTHER INFORMATION: cDNA human truncated WT1

<400> SEQUENCE: 10

| | |
|---|---|
| atggacttcc tcttgctgca ggacccggct tccacgtgtg tcccggagcc ggcgtctcag | 60 |
| cacacgctcc gctccgggcc tgggtgccta cagcagccag agcagcaggg agtccgggac | 120 |
| ccgggcggca tctgggccaa gttaggcgcc gccgaggcca gcgctgaacg tctccagggc | 180 |
| cggaggagcc gcgggcgtc cgggtctgag ccgcagcaaa tgggctccga cgtgcgggac | 240 |
| ctgaacgcgc tgctgcccgc cgtccccctcc ctgggtggcg gcggcggctg tgccctgcct | 300 |
| gtgagcggcg cggcgcagtg ggcgccggtg ctggactttg cgccccggg cgcttcggct | 360 |
| tacgggtcgt tgggcggccc cgcgccgcca ccggctccgc cgccaccccc gccgccgccg | 420 |
| cctcactcct tcatcaaaca ggagccgagc tggggcggcg cggagccgca cgaggagcag | 480 |
| tgcctgagcg ccttcactgt ccacttttcc ggccagttca ctggcacagc cggagcctgt | 540 |
| cgctacgggc ccttcggtcc tcctccgccc agccaggcgt catccggcca ggccaggatg | 600 |
| tttcctaacg cgccctacct gcccagctgc ctggagagcc agcccgctat cgcaatcag | 660 |
| ggttacagca cggtcacctt cgacgggacg cccagctacg gtcacacgcc ctcgcaccat | 720 |
| gcggcgcagt tccccaacca ctcattcaag catgaggat ccatgggcca gcagggctcg | 780 |
| ctgggtgagc agcagtactc ggtgccgccc ccggtctatg gctgccacac ccccaccgac | 840 |

```
agctgcaccg gcagccaggc tttgctgctg aggacgccct acagcagtga caatttatac    900
caaatgacat cccagcttga atgcatgacc tggaatcaga tgaacttagg agccaccttg    960
aagggagttg ctgctgggag ctccagctca gtgaaatgga cagaagggca gagcaaccac   1020
agcacagggt acgagagcga taaccacaca acgcccatcc tctgcggagc caatacaga   1080 atacacacgc acggtgtctt cagaggcatt cagtga                             1116
```

<210> SEQ ID NO 11
<211> LENGTH: 1893
<212> TYPE: DNA
<213> ORGANISM: Artificial Sequence
<220> FEATURE:
<223> OTHER INFORMATION: cDNA human MSLN

<400> SEQUENCE: 11

```
atggccttgc caacggctcg accctgttg gggtcctgtg gaccccgc cctcggcagc       60 ctcctgttcc tgctcttcag cctcggatgg gtgcagccct caggaccct ggctggagag    120 acagggcagg aggctgcgcc cctggacgga gtcctggcca acccacctaa catttccagc   180
ctctcccctc gccaactcct tggcttcccg tgtgcggagg tgtccggcct gagcacggag   240
cgtgtccggg agctggctgt ggccttggca cagaagaatg tcaagctctc aacagagcag   300
ctgcgctgtc tggctcaccg gctctctgag ccccccgagg acctgacgc cctcccattg    360 gacctgctgc tattcctcaa cccagatgcg ttctcgggc cccaggcctg cacccgtttc    420
ttctcccgca tcacgaaggc caatgtggac ctgctcccga ggggggctcc cgagcgacag    480
cggctgctgc ctgcggctct ggcctgctgg ggtgtgcggg ggtctctgct gagcgaggct   540
gatgtgcggg ctctgggagg cctggcttgc gacctgcctg ggcgctttgt ggccgagtcg   600
gccgaagtgc tgctaccccg gctggtgagc tgcccgggac cctggacca ggaccaacag    660 gaggcagcca gggcggctct gcagggcggg ggaccccct acggccccc gtcgacatgg    720 tctgtctcca cgatggacgc tctgcggggc ctgctgccg tgctgggcca gcccatcatc    780
cgcagcatcc gcagggcat cgtggccgcg tggcggcaac gctcctctcg ggacccatcc    840
tggcggcagc ctgaacggac catcctccgg ccgcggttcc ggcgggaagt ggagaagaca    900
gcctgtcctt caggcaagaa ggcccgcgag atagacgaga gcctcatctt ctacaagaag   960
tgggagctgg aagcctgcgt ggatgcgcc ctgctggcca cccagatgga ccgcgtgaac   1020
gccatcccct tcacctacga gcagctggac gtcctaaagc ataaactgga tgagctctac   1080
ccacaaggtt accccgagtc tgtgatccag cacctgggc acctcttcct caagatgagc   1140
cctgaggaca ttcgcaagtg aatgtgacg tccctggaga ccctgaaggc tttgcttgaa   1200
gtcaacaaag gcacgaaat gagtcctcag gctcctcggc ggcccctccc acaggtggcc   1260
accctgatcg accgctttgt gaagggaagg ggccagctag acaaagacac cctagacacc   1320
ctgaccgcct ctaccctgg gtacctgtgc tccctcagcc ccgaggagct gagctccgtg   1380
ccccccagca gcatctgggc ggtcaggccc caggacctgg acacgtgtga cccaaggcag   1440
ctggacgtcc tctatcccaa ggcccgcctt gctttccaga acatgaacgg tccgaatac   1500 ttcgtgaaga tccagtcctt cctgggtggg gccccacgg aggatttgaa ggcgctcagt   1560
cagcagaatg tgagcatgga cttggccacg ttcatgaagc tgcggacgga tgcggtgctg   1620
ccgttgactg tggctgaggt gcagaaactt ctgggaccc acgtgaggg cctgaaggcg   1680 gaggagcggc accgccggt gcgggactgg atcctacggc agcggcagga cgacctggac   1740
```

-continued

| | |
|---|---|
| acgctggggc tggggctaca gggcggcatc cccaacggct acctggtcct agacctcagc | 1800 |
| atgcaagagg ccctctcggg gacgccctgc ctcctaggac ctggacctgt tctcaccgtc | 1860 |
| ctggcactgc tcctagcctc caccctggcc tga | 1893 |

<210> SEQ ID NO 12
<211> LENGTH: 2109
<212> TYPE: DNA
<213> ORGANISM: Artificial Sequence
<220> FEATURE:
<223> OTHER INFORMATION: cDNA human CEA

<400> SEQUENCE: 12

| | |
|---|---|
| atggagtctc cctcggcccc tccccacaga tggtgcatcc cctggcagag gctcctgctc | 60 |
| acagcctcac ttctaacctt ctggaacccg cccaccactg ccaagctcac tattgaatcc | 120 |
| acgccgttca atgtcgcaga ggggaaggag gtgcttctac ttgtccacaa tctgccccag | 180 |
| catcttttg ctacagctg gtacaaaggt gaaagagtgg atggcaaccg tcaaattata | 240 |
| ggatatgtaa taggaactca acaagctacc ccagggcccg catacagtgg tcgagagata | 300 |
| atataccccca atgcatccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact caaacccgt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca atgtgaaaac cagaacccca | 660 |
| gtgagtgcca ggcgcagtga ttcagtcatc ctgaatgtcc tctatggccc ggatgccccc | 720 |
| accatttccc ctctaaacac atcttacaga tcaggggaaa atctgaacct ctcctgccac | 780 |
| gcagcctcta acccacctgc acagtactct tggtttgtca atgggacttt ccagcaatcc | 840 |
| acccaagagc tctttatccc caacatcact gtgaataata gtggatccta tacgtgccaa | 900 |
| gcccataact cagacactgg cctcaatagg accacagtca cgacgatcac agtctatgca | 960 |
| gagccaccca aaccccttca tcaccagcaac aactccaacc ccgtggagga tgaggatgct | 1020 |
| gtagccttaa cctgtgaacc tgagattcag aacacaacct acctgtggtg ggtaaataat | 1080 |
| cagagcctcc cggtcagtcc caggctgcag ctgtccaatg acaacaggac cctcactcta | 1140 |
| ctcagtgtca aaggaatga tgtaggaccc tatgagtgtg aatccagaa caattaagt | 1200 |
| gttgaccaca gcgacccagt catcctgaat gtcctatatg gcccagacga ccccaccatt | 1260 |
| tccccctcat acacctatta ccgtccaggg gtgaacctca gcctctcctg ccatgcagcc | 1320 |
| tctaacccac tgcacagta ttcttggctg attgatggga acatcagca acacacacaa | 1380 |
| gagctctta tctccaacat cactgagaag aacagcggac tctatacctg ccaggccaat | 1440 |
| aactcagcca gtggccacag caggactaca gtcaagacaa tcacagtctc tgcggagctg | 1500 |
| cccaagcct ccatctccag caacaactcc aaacccgtgg aggacaagga tgctgtggcc | 1560 |
| ttcacctgtg aacctgaggc tcagaacaca acctacctgt ggtgggtaaa tggtcagagc | 1620 |
| ctcccagtca gtcccaggct gcagctgtcc aatggcaaca gaccctcac tctattcaat | 1680 |
| gtcacaagaa atgacgcaag agcctatgta tgtggaatcc agaactcagt gagtgcaaac | 1740 |
| cgcagtgacc cagtcaccct ggatgtcctc tatgggccgg acacccccat catttccccc | 1800 |
| ccagactcgt cttaccttc gggagcgaac ctcaacctct cctgccactc ggcctctaac | 1860 |
| ccatccccgc agtattcttg gcgtatcaat gggataccgc agcaacacac acaagttctc | 1920 |

| | |
|---|---|
| tttatcgcca aaatcacgcc aaataataac gggacctatg cctgttttgt ctctaacttg | 1980 |
| gctactggcc gcaataattc catagtcaag agcatcacag tctctgcatc tggaacttct | 2040 |
| cctggtctct cagctggggc cactgtcggc atcatgattg agtgctggt tggggttgct | 2100 |
| ctgatatag | 2109 |

```
<210> SEQ ID NO 13
<211> LENGTH: 1683
<212> TYPE: DNA
<213> ORGANISM: Artificial Sequence
<220> FEATURE:
<223> OTHER INFORMATION: cDNA CMV pp65

<400> SEQUENCE: 13
```

| | |
|---|---|
| atggaatcca gggggaggag gtgtccggag atgatctcag tcctcggacc gattagcggt | 60 |
| cacgtgctca agcggtctt cagcagagga gacactccgg tgctgccgca cgaaacaagg | 120 |
| ctccttcaga cggggataca cgtgcgtgtg agtcagccca gcctgatcct cgtgtctcaa | 180 |
| tacacccctg acagcactcc ctgtcacaga ggggacaacc aactccaggt ccagcacacc | 240 |
| tacttcactg ggagcgaggt cgagaacgtc agcgtgaacg tgcacaaccc cacgggaaga | 300 |
| tcaatctgcc ctagccagga gcccatgagc atctacgtgt acgccctccc gctcaagatg | 360 |
| ctcaacatcc cctccatcaa cgtccaccac tatccctccg ctgccgaacg taaacaccga | 420 |
| cacttgccag ttgcggacgc cgtgatacac gcttcaggga agcagatgtg gcaagccagg | 480 |
| cttactgtga gtggactcgc ctggactagg caacagaacc agtggaagga gcccgacgtg | 540 |
| tactacacca gcgccttcgt gttccccaca aaagacgtcg cgctgcgaca tgtggtgtgc | 600 |
| gctcacgaac tggtgtgcag catggagaac acgcgagcga ccaagatgca ggtgatcggt | 660 |
| gaccagtacg tcaaggtgta cctggagagc ttctgcgagg atgtcccgtc cggaaagctg | 720 |
| ttcatgcacg tgaccctggg cagtgacgtt gaggaagacc tgaccatgac gcgtaacccg | 780 |
| cagcctttca tgagaccgca cgagaggaac ggattcaccg tcctgtgccc gaagaacatg | 840 |
| atcatcaagc ccggcaagat cagccacatc atgctcgacg tcgccttcac ctctcacgaa | 900 |
| cacttcgggc tgctgtgtcc gaagagcatt ccgggtctga gcatctcagg caacctgctg | 960 |
| atgaacgggc agcagatctt cctggaagtg caggccataa gggagaccgt ggaactgagg | 1020 |
| cagtacgatc ctgtggctgc cctgttcttc ttcgacatcg acctcttgct gcaaggggtc | 1080 |
| ccacagtata gcgaacaccc caccttcacc tcccagtacc gtatccaggg caagctggag | 1140 |
| taccgacaca cttgggatag gcacgacgag ggtgccgctc aaggtgacga cgatgtttgg | 1200 |
| actagcggct ctgatagcga cgaagagctg gtgaccactg agcgcaaaac tccaagagtt | 1260 |
| acgggcggcg gcgcaatggc tggcgcctct acttccgcgg aaggaaaag gaaaagcgcg | 1320 |
| tctagcgcaa ctgcatgcac tgccggtgtg atgacaaggg ggagactgaa ggccgagagt | 1380 |
| acagtggctc cggaagagga taccgacgag gactctgaca cgagatcca accccgca | 1440 |
| gtgtttacgt ggccaccttg gcaagccggc atccttgcta gaaacctggt gcccatggtg | 1500 |
| gccacagtcc aaggccagaa cctgaagtac caggagttct tctgggacgc caacgacatc | 1560 |
| taccgtatct tcgccgaact tgaaggcgtc tggcagccgg cggctcaacc caaaggaga | 1620 |
| cgtcacagac aggacgcgct tcccggaccc tgtattgcct ctaccccaa gaaacaccgg | 1680 |
| ggc | 1683 |

```
<210> SEQ ID NO 14
```

<211> LENGTH: 1683
<212> TYPE: DNA
<213> ORGANISM: Artificial Sequence
<220> FEATURE:
<223> OTHER INFORMATION: cDNA mutated CMV pp65

<400> SEQUENCE: 14

```
atggaatcca gggggaggag gtgtccggag atgatctcag tcctcggacc gattagcggt      60
cacgtgctca aagcggtctt cagcagagga gacactccgg tgctgccgca cgaaacaagg     120
ctccttcaga cggggataca cgtgcgtgtg agtcagccca gcctgatcct cgtgtctcaa     180
tacaccoctg acagcactcc ctgtcacaga ggggacaacc aactccaggt ccagcacacc     240
tacttcactg ggagcgaggt cgagaacgtc agcgtgaacg tgcacaaccc cacgggaaga     300
tcaatctgcc ctagccagga gcccatgagc atctacgtgt acgccctccc gctcaagatg     360
ctcaacatcc cctccatcaa cgtccaccac tatccctccg ctgccgaacg taaacaccga     420
cacttgccag ttgcggacgc cgtgatacac gcttcaggga agcagatgtg gcaagccagg     480
cttactgtga gtggactcgc ctggactagg caacagaacc agtggaagga gcccgacgtg     540
tactacacca gcgccttcgt gttccccaca aaagacgtcg cgctgcgaca tgtggtgtgc     600
gctcacgaac tggtgtgcag catggagaac acgcgagcga ccaagatgca ggtgatcggt     660
gaccagtacg tcaaggtgta cctggagagc ttctgcgagg atgtcccgtc cggaaagctg     720
ttcatgcacg tgaccctggg cagtgacgtt gaggaagacc tgaccatgac gcgtaacccg     780
cagcctttca tgagaccgca cgagaggaac ggattcaccg tcctgtgccc gaagaacatg     840
atcatcaagc ccgcaagat cagccacatc atgctcgacg tcgccttcac ctctcacgaa     900
cacttcgggc tgctgtgtcc gaagagcatt ccgggtctga gcatctcagg caacctgctg     960
atgaacggga gcagatcttt cctggaagtg caggccataa gggagaccgt ggaactgagg    1020
cagtacgatc ctgtggctgc cctgttcttc ttcgacatcg acctcttgct gcaaaggggt    1080
ccacagtata gcgaacaccc caccttcacc tcccagtacc gtatccaggg caagctggag    1140
taccgacaca cttgggatag gcacgacgag ggtgccgctc aaggtgacga cgatgtttgg    1200
actagcggct ctgatagcga cgaagagctg gtgaccactg agcgcaaaac tccaagagtt    1260
acgggcggcg gcgcaatggc tggcgcctct acttccgcgg aaggaacaga gaaaagcgcg    1320
tctagcgcaa ctgcatgcac tgccggtgtg atgacaaggg ggagactgaa ggccgagagt    1380
acagtggctc cggaagagga taccgacgag gactctgaca cgagatccaa caccccgca    1440
gtgtttacgt ggccaccttg gcaagccggc atccttgcta gaaacctggt gcccatggtg    1500
gccacagtcc aaggccagaa cctgaagtac caggagttct tctgggacgc caacgacatc    1560
taccgtatct tcgccgaact tgaaggcgtc tggcagccgg cggctcaacc caaaaggaga    1620
cgtcacagac aggacgcgct tcccggaccc tgtattgcct ctaccccaa gaaacaccgg    1680
ggc                                                                 1683
```

<210> SEQ ID NO 15
<211> LENGTH: 1608
<212> TYPE: DNA
<213> ORGANISM: Artificial Sequence
<220> FEATURE:
<223> OTHER INFORMATION: cDNA mutated truncated CMV pp65

<400> SEQUENCE: 15

```
atggaatcca gggggaggag gtgtccggag atgatctcag tcctcggacc gattagcggt      60
cacgtgctca aagcggtctt cagcagagga gacactccgg tgctgccgca cgaaacaagg     120
```

-continued

```
ctccttcaga cggggataca cgtgcgtgtg agtcagccca gcctgatcct cgtgtctcaa    180
tacacccctg acagcactcc ctgtcacaga ggggacaacc aactccaggt ccagcacacc    240
tacttcactg ggagcgaggt cgagaacgtc agcgtgaacg tgcacaaccc cacgggaaga    300
tcaatctgcc ctagccagga gcccatgagc atctacgtgt acgccctccc gctcaagatg    360
ctcaacatcc cctccatcaa cgtccaccac tatccctccg ctgccgaacg taaacaccga    420
cacttgccag ttgcggacgc cgtgatacac gcttcaggga agcagatgtg gcaagccagg    480
cttactgtga gtggactcgc ctggactagg caacagaacc agtggaagga gcccgacgtg    540
tactacacca gcgccttcgt gttccccaca aaagacgtcg cgctgcgaca tgtggtgtgc    600
gctcacgaac tggtgtgcag catggagaac acgcgagcga ccaagatgca ggtgatcggt    660
gaccagtacg tcaaggtgta cctggagagc ttctgcgagg atgtcccgtc cggaaagctg    720
ttcatgcacg tgaccctggg cagtgacgtt gaggaagacc tgaccatgac gcgtaacccg    780
cagcctttca tgagaccgca cgagaggaac ggattcaccg tcctgtgccc gaagaacatg    840
atcatcaagc ccggcaagat cagccacatc atgctcgacg tcgccttcac ctctcacgaa    900
cacttcgggc tgctgtgtcc gaagagcatt ccgggtctga gcatctcagg caacctgctg    960
atgaacgggc agcagatctt cctggaagtg caggccataa gggagaccgt ggaactgagg   1020
cagtacgatc ctgtggctgc cctgttcttc ttcgacatcg acctcttgct gcaaaggggt   1080
ccacagtata gcgaacaccc caccttcacc tcccagtacc gtatccaggg caagctggag   1140
taccgacaca cttgggatag gcacgacgag ggtgccgctc aaggtgacga cgatgtttgg   1200
actagcggct ctgatagcga cgaagagctg gtgaccactg agcgcaaaac tccaagagtt   1260
acgggcggcg gcgcaatggc tggcgcctct acttccgcgg gaaggaacag gaaaagcgcg   1320
tctagcgcaa ctgcatgcac tgccggtgtg atgacaaggg ggagactgaa ggccgagagt   1380
acagtggctc cggaagagga taccgacgag gactctgaca acgagatcca caacccccgca   1440
gtgtttacgt ggccaccttg gcaagccggc atccttgcta gaaacctggt gcccatggtg   1500
gccacagtcc aaggccagaa cctgaagtac caggagttct tctgggacgc caacgacatc   1560
taccgtatct tcgccgaact tgaaggcgtc tggcagccgg cggctcaa               1608
```